United States Patent [19]
Singh et al.

[11] Patent Number: 5,959,123
[45] Date of Patent: *Sep. 28, 1999

[54] 3,4-DISUBSTITUTED AZETIDIN-2-ONE DERIVATIVES USEFUL AS CYSTEINE PROTEINASE REGULATORS

[75] Inventors: Rajeshwar Singh; Nian E. Zhou; Deqi Guo, all of Edmonton; Ronald G. Micetich, Sherwood Park, all of Canada

[73] Assignee: Synphar Laboratories, Inc., Alberta, Canada

[ * ] Notice: This patent is subject to a terminal disclaimer.

[21] Appl. No.: 08/935,258

[22] Filed: Sep. 22, 1997

Related U.S. Application Data

[60] Provisional application No. 60/026,516, Sep. 23, 1996.
[51] Int. Cl.$^6$ .................................................. C07D 205/00
[52] U.S. Cl. ......................... 548/953; 548/950; 514/210; 540/200
[58] Field of Search ............................. 540/200; 514/19; 548/950, 953

[56] References Cited

FOREIGN PATENT DOCUMENTS

| | | |
|---|---|---|
| 0021678 | 6/1980 | European Pat. Off. . |
| 0053815 | 4/1981 | European Pat. Off. . |
| 0053816 | 4/1981 | European Pat. Off. . |
| 0050965 | 10/1981 | European Pat. Off. . |
| 0093376 | 4/1983 | European Pat. Off. . |
| WO 96/32408 | 3/1996 | WIPO . |

OTHER PUBLICATIONS

*Monocyclic B–lactam antibiotics produced by bacteria*, Sykes et al., vol. 291, Jun. 11, 1981, pp. 489–491 XP 002050350.

*Synthesis and antibacterial activity of C4 substituted monobactams*, Arnould et al., Eur. J. Med Chem (1992) 27, 131–140, XP 002050351.

*4-Alkylated Monobactams– Chiral Synthesis and Antibacterial Activity*, Cimarusti et al, vol. 39, No. 15. pp. 2577 to 2589, 1983 XP 002050352.

Primary Examiner—Cecilia J. Tsang
Assistant Examiner—David Lukton
Attorney, Agent, or Firm—Nikaido Marmelstein Murray & Oram LLP

[57] ABSTRACT

The present invention is based on the discovery that certain 3,4-disubstituted-azetidin-2-one derivatives exhibit excellent cysteine proteinase inhibitory activity which can be used for treatment of different diseases such as muscular dystrophy, myocardial infarction, bone resorption, arthritis, cancer metastasis, pulmonary emphysema, septic shock, cerebral ischemia, memory function, Alzheimer and cataract, malaria, glomerular basement membrane degradation, bacterial infection, inflammatory diseases, parasitic infections, and viral infections. In accordance to the present invention, there is provided a 3,4-disubstituted-azetidin-2-one derivatives of formula I, wherein $R_1$, $R_2$ and $R_3$ are as defined herein, or a pharmaceutically acceptable salt thereof.

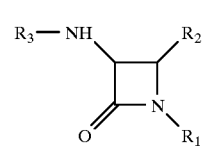

29 Claims, No Drawings

3,4-DISUBSTITUTED AZETIDIN-2-ONE DERIVATIVES USEFUL AS CYSTEINE PROTEINASE REGULATORS

This application claims priority of U.S. Provisional patent application Ser. No. 60/026,516, filed Sep. 23, 1996.

BACKGROUND OF THE INVENTION

Cysteine proteinases containing a highly reactive cysteine residue with a free thiol group at the active site have been known as playing an important role in certain conditions distinguished by aberrant protein turnover such as: muscular dystrophy (Am. J. Pathol. 1986, 122, 193–198; Am. J. Pathol. 1987, 127, 461–466), myocardial infarction (J. Am. Coll. Cardiol. 1983, 2, 681–688), bone resorption (Biochem. J. 1991, 279, 167–274; J. Biol. Chem. 1996, 271, 2126–2132; and Biochem. Biophys. Acta 1992, 1116, 57–66), arthritis (Arthritis Rheumatism 1994, 37, 236–247; and Biochem. Pharmacol. 1992, 44, 1201–1207), cancer metastasis (Cancer Metastasis Rev. 1990, 9, 333–352), pulmonary emphysema (Am. Rev. Respir. Dis. 1975,111, 579–586), septic shock (Immunol. Today 1991, 11, 404–410, Biochemistry 1994, 33, 3934–3940), cerebral ischemia, memory function, Alzheimer and cataract (TIPS 1994, 15, 412–419, Bioorg. Med. Chem. Lett. 1995, 4, 387–392, Proc. Natl. Acad. Sci. USA 1991, 88, 10998–11002), malaria (J. Med. Chem. 1995, 38, 5031–5037), glomerular basement membrane degradation (Biochem. Bioph. Acta 1989, 990, 246–251), bacterial infection (Nature 1989, 337, 385–386), inflammatory diseases (Protein Science 1995, 4, 3–12), parasitic infections (Annu. Rev. Microbiol. 1993, 47 821–853; Parasitol. Today 1990, 6, 270–275), and viral infections (Biochem. 1992, 31, 7862–7869).

A variety of cysteine proteinase have been shown to be present in mammalian tissue. The most notable of these proteinase are the lysosomal cathepsins (cathepsin B, H, S, K and L) and the cytoplasmic $Ca^{2+}$ dependent enzymes, the calpains. These enzymes are, therefore, excellent targets for the development of specific inhibitors as possible therapeutic agents.

Cysteine proteinase are inhibited by several types of peptide derived inhibitors such as peptidyl aldehyde (Eur. J. Biochem. 1982, 129, 3341), chloromethyl ketone (Acta Biol. Med. Ger. 1981, 40, 1503–151 1), diazomethyl ketone (Biochemistry 1977,16, 5857–5861), monofluoromethyl ketone (Biochemical Pharmacology 1992 44,1201–1207), acyloxy methyl ketone (J. Med. Chem. 1994, 37, 1833–1840), O-acyl hydroxamates (Biochem. Biophy. Research Communications 1988, 155, 1201–1206), methyl sulphonium salts (J. Biol. Chem. 1988,263, 2768–2772) and epoxy succinyl derivatives (Agric. Biol. Chem. 1978, 42, 523–527) without significantly inhibiting other classes of proteinases.

Unfortunately, the effectiveness in vivo of such compounds is not as much as expected on the basis of in vitro inhibitory activity, and there exits a continuing need to develop new cysteine proteinase inhibitors with high selectivity and lower toxicity.

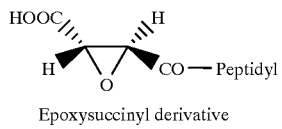

Peptidyl-CO—Y

Y = H, $CH_2Cl$, $CHN_2$, $CH_2F$, $CH_2OCOAr$, NHOCOR, $CH_2S$—$(CH_3)_2$

Epoxysuccinyl derivative

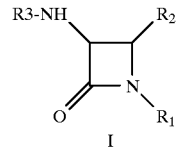

I

Our laboratory has been actively involved in search of novel types of cysteine proteinase inhibitors with high selectivity among cysteine proteinase class of enzymes. We have found that a novel class of compounds having natural peptidyl group at C-3 of reactive group 3-amino-4-substituted azetidin-2-one, represented by formula 1, exhibit an excellent cysteine proteinase regulatory (e.g., inhibitory) activity and selectivity among cysteine proteinases, which is reported in U.S. patent application Ser. No. 08/415,055.

SUMMARY OF THE INVENTION

In accordance with the present invention, there are provided 3,4-disubstituted azetidin-2-one derivatives which exhibit excellent cysteine proteinase regulatory activity and which can be used for treatment of different diseases such as muscular dystrophy, myocardial infarction, bone resorption, arthritis, cancer metastasis, pulmonary emphysema, septic shock, cerebral ischemia, memory function, Alzheimer and cataract, malaria, glomerular basement membrane degradation, bacterial infection, inflammatory diseases, parasitic infections, and viral infections.

In accordance with the present invention, there are provided 3,4-disubstituted azetidin-2-one derivatives of formula I and pharmaceutically acceptable salts thereof:

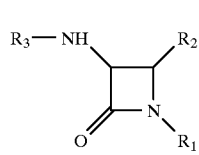

I wherein
$R_1$ is
hydrogen; or
—$SO_3^-M^+$ wherein M is a hydrogen atom, a metal ion which is selected from sodium, potassium, magnesium, and calcium, or $N^+(R_4)_4$ wherein $R_4$ is a $C_1$–$C_6$ alkyl group.
$R_2$ is
(a) a group —$OCOR_5$ wherein $R_5$ is
  (i) a $C_1$–$C_6$ alkyl group,
  (ii) a $C_2$–$C_6$ alkenyl group,
  (iii) a $C_2$–$C_6$ alkynyl group,
  (iv) a $C_3$–$C_6$ cycloalkyl group,
  (v) a phenyl group,
  (vi) a naphthyl group, or
  (vii) a monocyclic or bicyclic heterocyclic group, which group (i), (ii), (iii), (iv), (v), (vi), or (vii) is unsubstituted or substituted by 1, 2 or 3 substituents independently selected from
  hydroxy, halogen,
carboxy,
$C_1$–$C_4$ alkyl (which is unsubstituted or substituted at least once with carboxy and/or amino),
$C_1$–$C_2$ alkoxy,
amino,
cyano, and
phenyl and monocyclic or bicyclic heterocyclic groups, which phenyl and heterocyclic groups are unsubstituted or substituted by 1 or 2 substituents independently selected from
hydroxy,
halogen,
carboxy,
$C_1$–$C_4$ alkyl,
$C_1$–$C_2$ alkoxy,
amino, and
cyano;
or (b) a group —$XR_5$ wherein X is selected from the group consisting of O, S, SO, and $SO_2$, and $R_5$ is as defined above;

$R_3$ is selected from the group consisting of D- or L-phenyl glycine, D- or L-t-butyl alanine, D- or L-homophenyl alanine, D- or L-pyridyl alanine, D- or L-thienyl alanine, D- or L-naphthyl alanine, D- or L-methoxy phenyl alanine, D- or L-halo phenyl alanine, D- or L-$\epsilon$-nitro arginine, D- or L-citrulline, D- or L-2-indoline carboxylic acid, D- or L-cycloalkyl glycine (e.g., cyclopentyl glycine), D- or L-4-hydroxy-3-nitro-phenylalanine, D- or L-4-amino-3,5-diiodophenylalanine, D- or L-hydroxy-3,5-diiodo-phenylalanine, D- or L-4-hydroxy-3,5-dibromo-phenylalanine, D- or L-$\beta$-(3-benzothienyl)-alanine, D- or L-3,4(methylenedioxy)phenylalanine, D- or L-3,4(ethylenedioxy)phenylalanine, D- or L-4,4-biphenylalanine, D- or L-3,4-dichlorophenylalanine, D- or L-4-iodophenylalanine, D- or L-4-nitrophenylalanine, D- or L-pentafluorophenylalanine, D- or L-4-thiazolylalanine, D- or L-3-trifluoromethylphenylalanine, D- or L-4-trifluoromethylphenylalanine, D- or L-3-sulfamoyl-alanine, D- or L-t-butyloxy alanine, D- or L-1-t-butyloxymethylalanine, D- or L-trimethylalanine, D- or L-3,4-diisopropyloxphenylalanine, D- or L-propyl alanine, and D- or L-ethyl alanine, in which the $NH_2$ of any of the above groups is unsubstituted or substituted once or twice with $R_7$ wherein $R_7$ is —$COOR_5$, —$COR_5$, —$SO_2R_5$, or —$COR_{14}$ wherein $R_5$ is as defined above and $R_{14}$ is amino group which is unsubstituted or substituted at least once with $C_1$–$C_6$ alkyl group which is unsubstituted or substituted at least once with 1 or 2 substitutents selected from hydroxy, halogen, cyano, amino, heterocycle, and phenyl (wherein the heterocycle or phenyl is unsubstituted or substituted at least once by 1 or 2 substituents selected from halogen, hydroxy, cyano, carboxy and amino).

In a preferred aspect of the present invention, there are provided 3,4-disubstituted azetidin-2-one derivatives of formula I and pharmaceutically acceptable salts thereof:

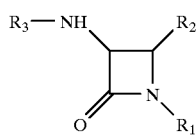

I wherein
$R_1$ is
hydrogen; or

—$SO_3^-M^+$ wherein M is a hydrogen atom, a metal ion which is selected from sodium, potassium, magnesium, and calcium, or $N^+(R_4)_4$ wherein $R_4$ is a $C_1$–$C_6$ alkyl group.

$R_2$ is
—$OCOR_5$ wherein $R_5$ is (i) a $C_1$–$C_6$ alkyl group which is unsubstituted or substituted at least once by 1 or 2 substitutents selected from hydroxy, halogen, and amino, or (ii) a phenyl group which is unsubstituted or substituted at least once by 1–3 substituents selected from hydroxy, halogen, $C_1$–$C_4$ alkyl group, $C_1$–$C_2$ alkoxy group, and cyano; or —$XR_6$ wherein X is O, S, SO, or $SO_2$; $R_6$ is (i) a $C_1$–$C_6$ alkyl group which is unsubstituted or substituted at least once by 1 or 2 substitutents selected from hydroxy, halogen, amino and phenyl (ii) a $C_3$–$C_6$ cycloalkyl group, (iii) a phenyl group which is unsubstituted or substituted at least once by 1–3 substituents selected from hydroxy, halogen, carboxy, $C_1$–$C_4$ alkyl group (which is unsubstituted or substituted with carboxy, amino or both), $C_1$–$C_2$ alkoxy group, cyano and heterocycle group, or (iv) naphthyl group which is unsubstituted or substituted at least once by 1–3 substituents selected from hydroxy, halogen, carboxy, $C_1$–$C_4$ alkyl group (which is unsubstituted or substituted at least once with carboxy, amino or both), $C_1$–$C_2$ alkoxy group and cyano;

$R_3$ is selected from a-amino acid residues of $\alpha$-amino acids, the $NH_2$ of which is unsubstituted or substituted once or twice with $R_7$ as defined below. The term "amino acid residue" used herein refers to the remaining group after the removal of the hydroxy group from a carboxy group of an amino acid. According to the present invention, the $\alpha$-amino acid can be selected from the group consisting of: D- or L-phenyl glycine, D- or L-t-butyl alanine, D- or L-homophenyl alanine, D- or L-pyridyl alanine, D- or L-thienyl alanine, D- or L-naphthyl alanine, D- or L-methoxy phenyl alanine, D- or L-halo phenyl alanine, D- or L-$\epsilon$-nitro arginine, D- or L-citrulline, D- or L-2-indoline carboxylic acid, D- or L-cycloalkyl glycine (e.g., cyclopentyl glycine), D- or L-4-hydroxy-3-nitro-phenylalanine, D- or L-4-amino-3,5-diiodophenylalanine, D- or L-4-hydroxy-3,5-diiodo-phenylalanine, D- or L-4-hydroxy-3,5-dibromo-phenylalanine, D- or L-$\beta$-(3-benzothienyl)-alanine, D- or L-3,4(methylenedioxy)phenylalanine, D- or L-3,4 (ethylenedioxy)phenylalanine, D- or L-4,4'-biphenylalanine, D- or L-3,4-dichlorophenylalanine, D- or L-4-iodophenylalanine, D- or L-4-nitrophenylalanine, D- or L-pentafluorophenylalanine, D- or L-4-thiazolylalanine, D- or L-3-trifluoromethylphenylalanine, D- or L-4-trifluoromethylphenylalanine, D- or L- 3-sulfamoyl-alanine, D- or L-t-butyloxy alanine, D- or L-1-t-butyloxymethylalanine, D- or L-trimethylalanine, D- or L-3,4-diisopropyloxyphenylalanine, D- or L-propyl alanine, and D- or L-ethyl alanine, in which the $NH_2$ of any of the above groups is unsubstituted or substituted once or twice with $R_7$ wherein $R_7$ is
—$COOR_8$ wherein $R_8$ is a $C_1$–$C_6$ alkyl group which is unsubstituted or substituted at least once with phenyl group,
—$COR_9$ wherein $R_9$ is
(i) a $C_1$–$C_6$ alkyl group which is unsubstituted or substituted at least once by 1 or 2 substitutents selected from hydroxy, halogen, cyano, amino, heterocycle, or phenyl (wherein the heterocycle or phenyl is unsubstituted or substituted at least once by 1 or 2 substituents selected from halogen, hydroxy, cyano, carboxy and amino); (ii) a heterocycle which may be mono or bicyclic or (iii)

amino group which is unsubstituted or substituted at least once with $C_1$–$C_6$ alkyl group which is unsubstituted or substituted at least once with 1 or 2 substitutents selected from hydroxy, halogen, cyano, amino, heterocycle, and phenyl (wherein the heterocycle or phenyl is unsubstituted or substituted at least once by 1 or 2 substituents selected from halogen, hydroxy, cyano, carboxy and amino); or $SO_2R_{10}$ wherein $R_{10}$ is (i) a $C_1$–$C_6$ alkyl group (ii) a $C_2$–$C_4$ alkenyl group which is unsubstituted or substituted at least once with heterocycle or phenyl, or (iii) a phenyl group which is unsubstituted or substituted at least once by 1–3 substituents selected from hydroxy, halogen, carboxy, $C_1$–$C_4$ alkyl group, $C_1$–$C_2$ alkoxy group and cyano.

The pharmaceutically acceptable salts of formula I are selected from salts of sodium, potassium, magnesium, calcium, hydrogen chloride, tartaric acid, succinic acid, fumaric acid or p-toluenesulfonic acid.

Examples of $C_1$–$C_6$ alkyl group as substituents in $R_4$, $R_5$, $R_6$, $R_8$, $R_9$, or $R_{10}$ are straight or branched chain alkyl group having 1–6 carbon atoms such as methyl, ethyl, propyl, 1-methylethyl, butyl, 1-methylpropyl, 2-methylprop-1-yl, 2-methylprop-2-yl, pentyl, 3-methylbutyl, hexyl and the like.

Examples of halogen atoms as substitutents in $R_5$, $R_6$, $R_9$, or $R_{10}$ are fluorine, chlorine, bromine or iodine.

Examples of $C_2$–$C_6$ alkenyl group as defined in $R_5$ and $R_{10}$ are alkenyl group having 2–4 carbon atoms such as ethenyl, 1-propenyl, 2-propenyl, 1-butenyl, 3-butenyl and the like.

Examples of $C_2$–$C_6$ alkynyl group as defined in $R_5$ and $R_{10}$ are alkynyl group having 2-4 carbon atoms such as ethynyl, 1-propynyl, 2-propynyl, 1-butynyl, 3-butynyl and the like.

Examples of $C_3$–$C_6$ cycloalkyl group as defined in $R_5$ and $R_6$ are cyclopropyl, cyclobutyl, cyclopentyl, or cyclohexyl.

As used herein "monocyclic heterocyclic" means a 5- or 6-membered aromatic or non-aromatic heterocyclic group containing 1, 2, 3 or 4 heteroatoms selected from O, S or N; and "bicyclic heterocyclic" means a monocyclic heterocyclic as defined above which is fused to a second 5- or 6-membered carbocyclic or 5- or 6-membered heterocyclic ring.

Examples of preferred heterocyclic group or substituent as defined in $R_5$, $R_6$, $R_9$, or $R_{10}$ include $C_2$–$C_{11}$ mono or bicyclic heterocyclic group which may have 1–3 heteroatoms selected from nitrogen, sulphur or oxygen such as thiophene, pyridine, 1,2,3-triazole, 1,2,4-triazole, quinoline, benzofuran, benzothiophene, morpholine, thiomorpholine, piperizine, piperidine and the like.

Examples of $C_1$–$C_6$ alkyl group as substituents in $R_5$, $R_6$, $R_9$, or $R_{10}$ are methyl, ethyl, propyl, 2-methyl propyl, butyl, 1,1-dimethyl ethyl and the like.

Examples of $C_1$–$C_2$ alkoxy group as substituents in $R_5$, $R_6$, $R_9$, or $R_{10}$ are methoxy or ethoxy.

The term "amino acid residue" used herein refers to the remaining group after the removal of the hydroxy group from a carboxy group of an amino acid.

The azetidinone nucleus carries two asymmetric carbon atoms at position 3 and 4, and can exist as 4-diastereoisomers. In general, the preferred isomer is that in which the hydrogen atoms at C3 and C4 are cis to each other for superior inhibitory activity against different cysteine proteinase such as papain, Cathepsin B and Cathepsin L. Such diasterioisomers and their racemic mixtures are also included within use of the azetidinone derivatives as cystein proteinase inhibitor.

In accordance with preferred embodiments of the invention, there are provided 3,4-disubstituted-azetidin-2-one derivatives of formula I.

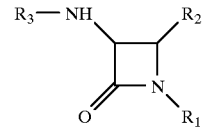

Wherein:

$R_1$ is selected from hydrogen, or sulphonic acid;

$R_2$ is selected from acetoxy, butyloxy, 2-carboxy ethyloxy, 2-aminoethyloxy, 2-fluoro ethoxy, cyclopentyloxy, cyclohexyloxy, cyclohexylthio, phenoxy, methyl phenoxy, naphthyloxy, morpholino phenyloxy, 2-hydroxy ethylthio, phenylthio, phenylsulphonyl, 4-(2-carboxy-2-amino ethyl)-phenoxy, 4-carboxy phenoxy, 3-carboxy phenoxy, 2-pyridylthio, 4-pyridylthio, benzyloxy and the like;

$R_3$ is selected from 1-benzyloxycarbonyl-2-indoline carboxylic acid, N-benzyloxy carbonyl phenyl glycine, N-benzyloxy carbonyl homophenyl alanine, N-benzyloxy carbonyl pyridyl alanine, N-benzyloxy carbonyl thienyl alanine, N-benzyloxy carbonyl naphthyl alanine, N-benzyloxy carbonyl halophenyl alanine, N-benzyloxy carbonyl naphthyl alanine, N-(3-phenyl propanoyl) naphthyl alanine, $N^\epsilon$-nitro arginine, N-(3-phenyl propanoyl) citrulline, N-benzylamino carbonyl naphthyl alanine, N-(2-phenyl-eth-1-en-sulphonyl)-naphthyl alanine, N-benzyloxycarbonyl-t-butyloxyalanine; N-benzyloxycarbonyl-t-butyloxymethyl alanine; N-benzyloxycarbonyl-t-butyl alanine; N-phenylpropionoyl-t-butyl alanine; N-phenylpropionoyl-trimethyl alanine; N-phenylpropionoyl-(3, 4-dimethoxyphenyl) alanine; N-phenylpropionoyl-(3,4-ethylenedioxyphenyl) alanine; N-benzyloxycarbonyl-3-benzothienyl alanine; N-benzyloxycarbonyl-(4,4'-biphenyl) alanine; N-benzyloxycarbonyl-(2-chlorophenyl)alanine; N-benzyloxycarbonyl-(4-chlorophenyl)alanine; N-benzyloxycarbonyl-(3,4-dichloro)-phenylalanine; N-benzyloxycarbonyl-(diphenyl) alanine; N-benzyloxycarbonyl-(2-fluoro) phenylalanine; N-benzyloxycarbonyl-(4-fluoro-phenyl) alanine; N-benzyloxycarbonyl-(3,4-difluoro-phenyl) alanine; N-benzyloxycarbonyl-(4-iodo-phenyl) alanine; N-benzyloxycarbonyl-2-(naphthyl) alanine; N-benzyloxycarbonyl-(4-nitro-phenyl) alanine; N-benzyloxycarbonyl-(pentafluorophenyl) alanine; N-benzyloxycarbonyl-(4-thiazolyl) alanine; N-benzyloxycarbonyl-3-(trifluoromethylphenyl) alanine; N-benzyloxycarbonyl-4-(trifluoromethylphenyl) alanine; N-benzyloxycarbonyl-(3-sulfamoyl) alanine; N-phenylpropionoyl-(3,4-methylenedioxyphenyl) alanine; N-phenylpropionoyl-(3,4-diisopropyloxyphenyl) alanine; N-benzyloxycarbonyl-propyl alanine; and N-benzyloxycarbonyl-ethyl alanine.

More specifically, the most preferred embodiments of the present invention include the following compounds:

(3S,4S)-3-(1-N-benzyloxycarbonyl-2-indolinecarbonyl)-amino-4-acetoxy-azetidin-2-one;

(3S,4S)-3-(N-benzyloxycarbonyl-D-phenylglycyl)-amino-4-acetoxy-azetidin-2-one;

(3S,4S)-3-(N-benzyloxycarbonyl-DL-phenylglycyl)-amino-4-acetoxy-azetidin-2-one;

(3S,4S)-3-(N-benzyloxycarbonyl-L-homophenylalanyl) amino-4-acetoxy-azetidin-2-one;

(3S,4S)-3-{N-benzyloxycarbonyl-β-(3-pyridyl)-L-alanyl}-amino-4-acetoxy-azetidin-2-one;
(3S,4S)-3-{N-benzyloxycarbonyl-β-(2-pyridyl)-L-alanyl}-amino-4-acetoxy-azetidin-2-one;
(3S,4S)-3-{N-benzyloxycarbonyl-β-(2-thienyl)-D L-alanyl}-amino-4-acetoxy-azetidin-2-one;
(3S,4S)-3-{N-benzyloxycarbonyl-β-(2-naphthyl)-L-alanyl}-amino-4-acetoxy-azetidin-2-one;
(3S,4S)-3-{N-benzyloxycarbonyl-β-(3-fluorophenyl)-L-alanyl}-amino-4-acetoxy-azetidin- 2-one;
(3S,4S)-3{N-benyloxycarbonyl-β-(4-methoxyphenyl)-L-alanyl}-amino-4-acetoxy-azetidin-2-one;
(3S,4S)-3-{N-benzyloxycarbonyl-β-(2-naphthyl)-L-alanyl}-amino-4-phenoxy-azetidin-2-one;
(3S,4S)-3{N-benzyloxycarbonyl-β-(2-naphthyl )-L-alanyl}-amino-4-(3-methyl phenoxy)-azetidin-2-one;
(3S,4R)-3-{N-benzyloxycarbonyl-β-(2-naphthyl)-L-alanyl}-amino-4-(3-methyl phenoxy)-azetidin-2-one;
(3S,4S)-3-{N-benzyloxycarbonyl-β-(2-naphthyl)-L-alanyl}-amino-4-(2-naphthoxy)-azetidin-2-one;
(3S,4R)-3{N-benzyloxycarbonyl-β-(2-naphthyl)-L-alanyl}-amino-4-(2-naphthoxy)-azetidin-2-one;
(3S,4S)-3-{N-benzyloxycarbonyl-β-(2-naphthyl)-L-alanyl}-amino-4-{3-(morpholin-4-yl)-phenoxy}-azetidin-2-one;
(3S,4R)-3-{N-benzyloxycarbonyl-β-(2-naphthyl)-L-alanyl}-amino-4-{3-(morpholin4-yl)-phenoxy}-azetidin-2-one;
(3S,4SR)-3-{N-(3-phenylpropionoyl)-β-(2-naphthyl)-L-alanyl}amino-4-phenylthio-azetidin-2-one;
(3S,4SR)-3-{N-(3-phenylpropionoyl)-β-(2-naphthyl)-L-alanyl}-amino-4-phenylsulphonyl-azetidin-2-one;
(3S,4SR)-3-{N-(3-phenylpropionoyl)-β-(2-naphthyl)-L-alanyl}amino-4-(2-hydroxy ethyl thio)-azetidin-2-one;
(3S,4SR)-3-{N-(3-phenylpropionoyl)-β-(2-naphthyl)-L-alanyl}amino-4-benzyloxy-azetidin-2-one;
(3S,4SR)-3-{N-(3-phenylpropionoyl)-β-(2-naphthyl)-L-alanyl}-amino-4-cyclohexyloxy-azetidin-2-one;
(3S,4S)-3-{N-(trans-2-phenyl-eth-1-enesulfonyl)-β-(2-naphthyl)-L-alanyl}-amino-4-acetoxy-azetidin-2-one;
(3S,4SR)-3-{N-(3-phenylpropionoyl)-β-(2-naphthyl)-L-alanyl}-amino-4-{4-(2S-2-amino-2-carboxyethyl)-phenoxy}-azetidin-2-one;
(3S,4S)-3{N-(benzylaminocarbonyl)-β-(2-naphthyl)-L-alanyl}-amino-4-acetoxy-azetidin- 2-one;
(3S,4SR)-3-{N-(benzylaminocarbonyl)-β-(2-naphthyl)-L-alanyl}-amino-4-{4-(2S-2-amino-2-carboxyethyl)-phenoxy}-azetidin-2-one;
(3S,4S)-3-{N-(3-phenylpropionoyl)-L-citrullinyl}-amino-4-acetoxy-azetidin-2-one; and
(3S,4S)-3-{N-(2-phenyl-eth-1-en-sulphonyl)-β-(2-naphthyl)-L-alanyl}-amino-4-acetoxy-azetidin-2-one;
(3S,4S)-3-{N$^\alpha$-(3-phenylpropionyl)-N$^\epsilon$-nitro-L-arginyl}-amino-4-acetoxy-azetidin-2-one;
(3S,4R)-3-(2S-2-benzyloxycarbonylamino-2-t-butyloxymethyl-acetamido)-4-phenoxy-azetidin-2-one;
(3S,4R)-3-[2S-2-benzyloxycarbonylamino-2-(1-t-butyloxyethyl)-acetamido]-4-phenoxy-azetidin-2-one;
(3S, 4S)-3-(2S-2-benzyloxycarbonylamino-2-t-butylmethyl-acetamido)-4-phenoxy-azetidin-2-one;
(3S,4S)-3-[2S-2-(3-phenylpropionoyl)amino-2-t-butylmethyl-acetamido]-4-phenoxy-azetidin-2-one;
(3S,4S)-3-[2S-2-(3-phenylpropionoyl)amino-2-t-butyl-acetamido]-4-phenoxy-azetidin-2-one;
(3S,4S)-3-[2S-2-(3-phenylpropionoyl) amino-2-(3, 4-dimethoxyphenyl) methyl-acetamido]-4-phenoxy-azetidin-2-one;
(3S,4S)-3-[2S-3-phenylpropionoyl) amino-2-(3,4-ethylenedioxyphenylmethyl)-acetamido]4-phenoxy-azetidin-2-one;
(3S,4S)-3-[2S-2-benzyloxycarbonylamino-2-(3-benzothienylmethyl)-acetamido]-4-phenoxy-azetidin-2-one;
(3S ,4S)-3-[2S-2-benzyloxycarbonylamino-2-(4,4'-biphenylmethyl)-acetamido]-4-phenoxy-azetidin-2-one;
(3S, 4S)-3-[2S-2-benzyloxycarbonylamino-2-(2-chlorophenylmethyl)-acetamido]-4-phenoxy-azetidin-2-one;
(3S, 4S)-3-[2S-2-benzyloxycarbonylamino-2-(4-chlorophenylmethyl)-acetamido]-4-phenoxy-azetidin-2-one;
(3S,4S)-3-[2S-2-benzyloxycarbonylamino-2-(3,4-dichlorophenylmethyl)-acetamido]- 4-phenoxy-azetidin-2-one;
(3S,4S)-3-[2S-2-benzyloxycarbonylamino-2-(diphenylmethyl) acetamido]-4-phenoxy-azetidin-2-one;
(3S,4S)-3-[2S-2-benzyloxycarbonylamino-2-(2-fluorophenylmethyl)-acetamido]-4-phenoxy-azetidin-2-one;
(3S,4S)-3-[2S-2-benzyloxycarbonylamino-2-(4-fluorophenylmethyl)-acetamido]-4-phenoxy-azetidin-2-one;
(3S,4S)-3-[2S-2-benzyloxycarbonylamino-2-(3,4-difluoro-phenylmethyl)-acetamido]-4-phenoxy-azetidin-2-one;
(3S,4S)-3-[2S-2-benzyloxycarbonylamino-2-(4-iodo-phenylmethyl)-acetamido]-4-phenoxy-azetidin-2-one;
(3S,4S)-3-[2S-2-benzyloxycarbonylamino-2-(naphth-1-yl)methyl-acetamido]-4-phenoxy-azetidin-2-one;
(3S,4S)-3-[2S-2-benzyloxycarbonylamino-2-(4-nitrophenylmethyl)-acetamido]-4-phenoxy-azetidin-2-one;
(3S,4S)-3-[2S-2-benzyloxycarbonylamino-2-(pentafluorophenyl-methyl)-acetamido]-4-phenoxy-azetidin-2-one;
(3S,4S)-3-[2S-2-benzyloxycarbonylamino-2-(4-thiazolylmethyl)-acetamido]-4-phenoxy-azetidin-2-one;
(3S,4S)-3-[2S-2-benzyloxycarbonylamino-2-(3-trifluoromethylphenyl-methyl)-acetamido]-4-phenoxy-azetidin-2-one;
(3S,4S)-3-[2S-2-benzyloxycarbonylamino-2-(3-sulfamoylmethyl)-acetamido]-4-phenoxy-azetidin-2-one;
(3S,4S)-3-[2S-2-(3-phenylpropionoyl) amino-2-(3,4-methylenedioxyphenylmethyl)-acetamido]4-phenoxy-azetidin-2-one;
(3S,4S)-3-[2S-2-(3-phenylpropionoyl) amino-2-(3,4-diisopropyloxyphenylmethyl)-acetamido]-4-phenoxy-azetidin-2-one;
(3S,4S)-3-[2S-2-benzyloxycarbonylamino-2-butyl-acetamido]-4-phenoxy-azetidin-2-one; and
(3S,4S)-3-[2S-2-benzyloxycarbonylamino-2-propyl-acetamido]-4-phenoxy-azetidin-2-one.

Compounds of formula I may be utilized for different diseases such as muscular dystrophy, myocardial infarction, bone resorption, arthritis, cancer metastasis, pulmonary emphysema, septic shock, cerebral ischemia, memory function, Alzheimer and cataract, malaria, glomerular basement membrane degradation, bacterial infection, inflammatory diseases, parasitic infections, and viral infections by inhibiting the cysteine proteinase in medicaments formulated with pharmaceutically acceptable carriers.

DESCRIPTION OF PREFERRED EMBODIMENTS

The present invention relates to the certain 3,4-disubstituted-azetidin-2-one derivatives having excellent cysteine proteinase inhibitory activity and selectivity among cysteine proteinase enzymes. The compounds of this invention are characterized by having hydrogen, ester (OCOR$_5$), ether ($OR_5$), thioether ($SR_5$), $SOR_5$, $SO_2R_5$ at position 4 of azetidin-2-one. Certain derivatives of formula I were prepared by the common intermediates II by reacting with substituted unnatural amino acids either in presence of dicyclohexylcarbidiimide (DCC) or acid chloride in presence of base, or activated ester according to techniques known in the art.

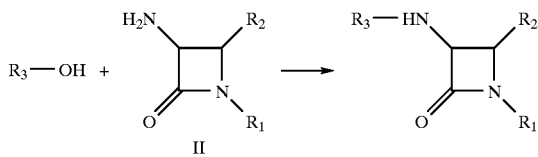

The preparation of compounds II were carried out by following the synthetic route as described in Eur. J. Med. Chem 1992, 27, 131–140, and Tetrahedron 1983, 39, 2577–2589, wherein $R_2$ is $OCOR_5$, and $R_3$ is an amino acid residue with a $COOR_8$ substituent. The definitions of $R_1$, $R_5$ and $R_8$ are the same as defined above.

Certain 3,4-disubstituted-azetidin-2-one derivatives of formula I wherein substititions at amino acid group are other than $COOR_5$, such as $COR_5$ or $SO_2R_5$, were prepared by following the synthetic route as shown in the scheme depicted below, wherein "AA" refers to an a-amino acid residue as disclosed herein. The $R_5$ groups are the same as defined above. The benzyloxycarbonyl substituted unnatural amino acid were desubstituted and resubstituted through amide bond by reacting with $R_5$–COOH either in presence of DCC or acid chloride in presence of base or anhydride in presence of base or activated ester, or through sulphonamide bond by reacting with $R_5SO_2Cl$ in presence of base or through urea bond by reacting with $R_{11}NCO$. $R_{11}$ is a $C_1$–$C_6$ alkyl group which may be substituted with phenyl or heterocyclic group.

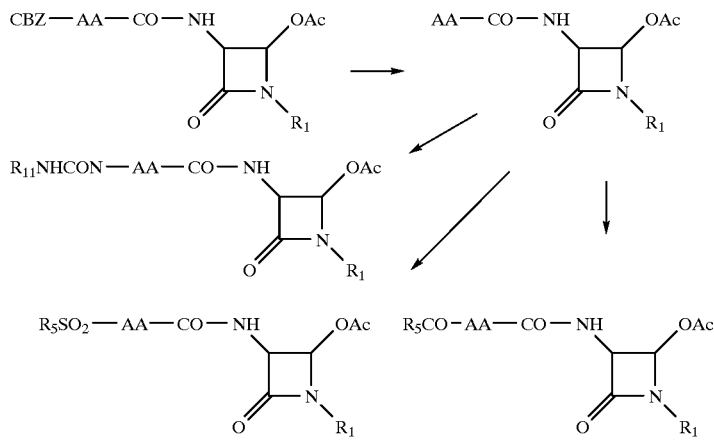

Certain 3,4-disubsubstituted-aztidin-2-one derivatives of formula I wherein $R_2$ is $XR_5$, wherein X is O or S, and $R_6$ is the same as defined above, were prepared by following the synthetic route as shown below starting from compound of formula I wherein $R_2$ is $OCOCH_3$ by reacting with $R_5XH$ in presence of lewis acids such as zinc acetate, zinc iodide, zinc chloride, titanium tetrachloride, palladium acetate, boron trifluoride, aluminium trichloride and the like or in presence of base such as sodium hydroxide. In certain cases where carboxy group as substituent in $R_5$ is substituted with $R_{12}$ such as diphenyl methyl or 1,1-dimethyl ethyl, or amino group as substituent in $R_5$ is substituted with $R_{13}$ such as benzyloxy carbonyl or 1,1-dimethyl ethoxy carbonyl, or both groups as substituents in $R_5$ together were desubstituted by hydrogenation or hydrolysis with acids.

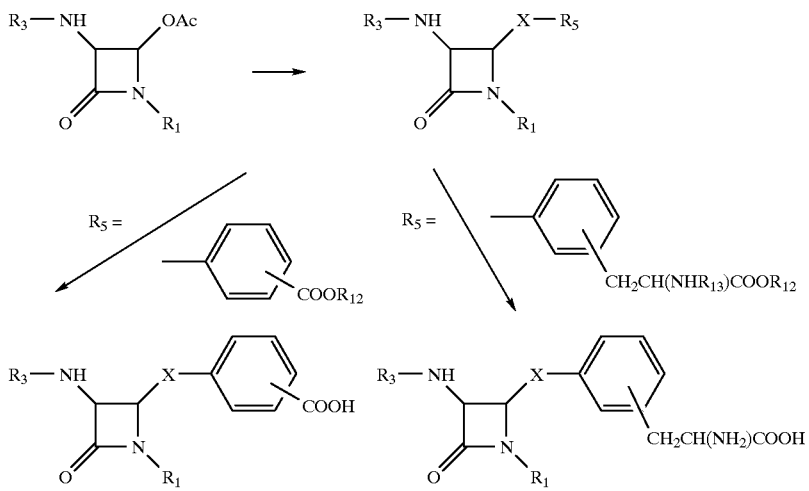

Certain 3,4-disubstituted-azetidin-2-one derivatives of formula I wherein $R_2$ is $SR_5$ were converted to $SOR_5$ or $SO_2R_5$ by oxidation with oxidizing agent selected from m-chloroperbenzoic acid, hydrogen peroxide. peracetic acid, potassium permanganate, magnese dioxide and the like. The synthetic route is outlined below.

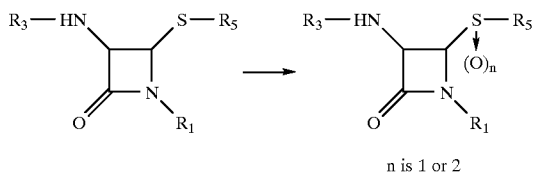

n is 1 or 2

3,4-Disubstituted-azetidin-2-one derivatives of formula I wherein $R_1$ is hydrogen can be converted to N-sulphonic acid by the sulphonation with pyridine-$SO_3$ or dimethylformamide-$SO_3$ complex by following the synthetic route as outlined below.

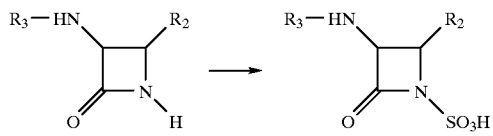

In the above descriptions, the reactants are reacted together with solvent at elevated or low temperatures for sufficient time to allow the reaction to proceed to completion. The reaction conditions will depend upon the nature and reactivity of the reactants. Wherever a base is used in a reaction, they are selected from triethylamine, pyridine, 4-dimethylaminopyridine, diisopropylethylamine, 1,5-diazabicyclo[4,3,0]non-5-ene, 1,8-diazabicyclo[5,4,0] undec-7-ene, sodium carbonate, potassium carbonate or cesium carbonate.

The solvent of choice for the reaction are selected from non reactive solvents depending on the reactants such as benzene, toluene, acetonitrile, tetrahydrofuran, ethanol, methanol, chloroform, ethyl acetate, methylene chloride, dimethyl formamide, dimethyl sulfoxide, hexamethyl phosphoric triamide, or the like. Solvent mixtures may also be utilized.

Reaction temperatures would generally be in the range of from $-70°$ C. to $150°$ C. The preferred molar ratio of reactants are 1:1 to 5.0. The reaction time is in the range of from 0.5 to 72 hours, depending on the reactants.

The desubstitution of N-substituted group is carried out either by hydrogenation or by hydrolysis with appropriate acids such as hydrochloric acid, trifluoroacetic acid or acetic acid in solvent such as methanol, ethanol, propanol or ethyl acetate. The hydrogenation reaction is usually carried out in the presence of a metal catalyst, such as Pd, Pt, or Rh, under normal pressure to high pressure.

The compounds of this invention, when used alone or in combination with other drugs as an agent for treating muscular dystrophy, myocardial infarction, bone resorption, arthritis, cancer metastasis, pulmonary emphysema, septic shock, cerebral ischemia, memory function, Alzheimer and cataract, malaria, glomerular basement membrane degradation, bacterial infection, inflammatory diseases, parasitic infections, and viral infections, in mammals including humans, may take pharmaceutical dosage forms including parenteral preparations such as injections, suppositories, aerosols and the like, and oral preparations such as tablets, coated tablets, powders, granules, capsules, liquids and the like. Injections are generally preferred. The above preparations are formulated in a manner known in the art.

For the formulation of solid preparations for oral administration, an excipient, and if desired, a binder, disintegrator, lubricant, coloring agent, corrigent, flavor etc. are added to the compound of the invention, and then tablets, coated tablets, granules, powders, capsules or the like are prepared in a conventional manner.

For the formulation of injections, a pH adjusting agent, buffer, stabilizer, isotonic agent, local anesthetic or the like is added to the active ingredient of the invention, and injections for subcutaneous, intramuscular or intravenous administration can be prepared in the conventional manner.

For the formulation of suppositories, a base, and if desired, a surfactant are added to the active ingredient of the invention, and the suppositories are prepared in a conventional manner.

The excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, schellac, sucrose, water, ethanol, propanol, carboxymethyl cellulose, potassium phosphate and the like, lubricants such as magnesium stearate, talc and the like, and further include additives such as usual known coloring agents, disintegrators and the like. Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives.

The amount of the compound I of the invention to be incorporated into the pharmaceutical composition of the invention varries with the dosage form, solubility and chemical properties of the compound, administration route, administration scheme and the like. Preferably the amount is about 1 to 25 w/w % in the case of oral preparations, and about 0.1 to about 5 w/w % in the case of injections which are parenteral preparations.

The dosage of the compound I of the invention is suitably determined depending on the individual cases taking symptoms, age and sex of the subject and the like into consideration. Usually the dosage in the case of oral administration is about 50 to 1500 mg per day for an adult in 2 to 4 divided doses, and the dosage in the case of injection, for example, by intravenous administration is 2 ml (about 1 to 100 mg) which is administered once a day for adults wherein the injection may be diluted with physiological saline or glucose injection liquid if so desired, and slowly administered over at least 5 minutes. The dosage in case of suppositories is about 1 to 1000 mg which is administered once or twice a day at an interval of 6 to 12 hours wherein the suppositories are administered by insertion into the rectum.

EXAMPLE 1

(3S,4S)-3-(1 -N-benzyloxycarbonyl-2-indolinecarbonyl)-amino-4-acetoxy-azetidin-2-one (1)

(3S,4S)-3-benzyloxycarbonylamino-4-acetoxy-azetidin-2-one (278 mg, 1 mmol) was hydrogenated with 300 mg of 10% palladium on activated carbon in 25 ml of ethyl acetate at 50 psi hydrogen pressure at room temperature for 1.5 hrs. After removal of catalyst by filtration, desubstituted (3S, 4S)-3-amino-4-acetoxy-azetidin-2-one in ethyl acetate was obtained.

To a solution of 1-benzyloxycarbonyl-2-indoline carboxylic acid (320 mg, 1.05 mmol) and triethylamine (106 mg, 1.05 mmol) in chloroform (20 ml), ethyl chloroformate (109 mg, 1 mmol) was added at −15° C. The reaction mixture was stirred at a bath temperature of −10 to 5° C. for 1 hr. Then a precooled solution of (3S,4S)-3-amino-4-acetoxy-azetidin-2-one in ethyl acetate was added at −15° C. and stirring was continued at a bath temperature of −15 to 5° C. for 1 hr. After removal of solvent, the residue was dissolved in ethyl acetate, washed with water, brine and dried over sodium sulfate. After removal of solvent, the residue was purified by silica gel column chromatography using hexane-ethyl acetate (1:3) as eluent and the title compound was obtained.

Yield: 71%.

m.p.: 196–197° C.

FAB-MS: 424 (MH$^+$), calcd for $C_{22}H_{21}N_3O_6$ 423 $^1$H NMR (DMSO-d$_6$), δ (ppm): 2.05 (3H, s), 2.90–3.05 (1 H, m), 3.45–3.65 (1 H m), 4.65 (1H, m), 4.90 (1H, m), 5.17 (2H, s), 5.70 (1H, s), 6.95–7.40 (9H, m), 8.95 (1H, d, J=8Hz), 9.20 (1H, s).

IR (KBr, cm$^{-1}$): 3300, 1800, 1745, 1716, 1670, 1541, 1485, 1408, 1363, 1275, 1223.

EXAMPLE 2

(3S,4S)-3-( N-benzyloxycarbonyl-D-phenylglycyl)-amino-4-acetoxy-azetidin- 2-one (2)

To a soulution of N-benzyloxycarbonyl-D-phenylglycine (285 mg, 1.0 mmol) and 1 -hydroxybenzotriazole (135 mg, 1.0 mmol) in THF (20 ml), DCC (206 mg, 1.0 mmol)/THF (10 ml) was added at 0° C. The reaction mixture was stirred at room temperature for 2 hrs and then cooled with an ice bath. The resulting DCU was removed by filtration. Then a precooled solution of (3S,4S)-3-amino-4-acetoxy-azetidin-2-one in ethyl acetate was added at −15° C. and the resulting mixture was stirred at a bath temperature of −15 to 5° C. for 1 hr and then at room temperature for 4 hrs. After removal of solvent, the residue was dissolved in ethyl acetate, washed with cold saturated NaHCO$_3$ solution, water, brine and dried over sodium sulfate. after removal of solvent, the residue was purified by silica gel column chromatography using hexane-ethyl acetate (1:2) as eluent and the title compound was obtained.

Yield: 71%.

m.p.: 181–182° C.

FAB-MS: 412 (MH$^+$), calcd for $C_{21}H_{21}N_3O_6$ 411

$^1$H NMR (DMSO-d$_6$), δ (ppm): 2.07 (3H, s), 4.61 (1 H, d, J=8 Hz), 5.05 (2H, s), 5.25 (1H, d, J=8.3 Hz), 5.71 (1H, s), 7.25–7.45 (10H, m), 8.06 (1H, d, J=8.3 Hz), 8.99 (1H, d, J=8 Hz), 9.20 (1 H, s).

IR (KBr, cm$^{-1}$): 3375, 1796, 1749, 1721, 1690, 1663, 1530, 1505, 1373, 1328, 1250, 1228.

EXAMPLE 3

(3S,4S)-3-(N-benzyloxycarbonyl-DL-phenylglycyl)-amino-4-acetoxy-azetidin-2-one (3)

By a similar method as described in example 2, the title compound was obtained by reacting N-benzyloxycarbonyl-DL-phenylglycine with (3S,4S)-3-amino-4-acetoxy-azetidin-2-one.

Yield: 50%.

m.p.: 145–146° C.

FAB-MS: 412 (MH$^+$), calcd for $C_{21}H_{21}N_3O_6$ 411

$^1$H NMR (DMSO-d$_6$), δ (ppm): 2.07 (3H, s), 4.66 (1H, d, J=8.4 Hz), 5.05 (2H, s), 5.25 (1H, d, J=8.4 Hz), 5.71 (1H, s), 7.25–7.45 (10H, m), 8.06 (1H, d, J=8.4 Hz), 8.97 (1H, m), 9.21 (1H, s).

IR (KBr, cm$^{-1}$): 3375, 1799, 1743, 1688, 1660, 1533, 1372, 1324, 1250, 1226.

EXAMPLE 4

(3S,4S)-3-(N-benzyloxycarbonyl-L-homophenylalanyl)-amino-4-acetoxy-azetidin-2-one (4)

By a similar method as described in example 1, the title compound was obtained by reacting N-benzyloxycarbonyl-L-homophenylalanine with (3S,4S)-3-amino-4-acetoxy-azetidin-2-one.

Yield: 45%.

m.p.: 180–181° C.

FAB-MS: 440 (MH$^+$), calcd for $C_{23}H_{25}N_3O_6$ 439

$^1$H NMR (DMSO-d$_6$), δ (ppm): 1.75–1.95 (2H, m), 2.08 (3H, s), 2.60 (2H, m), 4.04 (1H, m), 4.65 (1H, d, J=8 Hz), 5.06 (2H, m), 5.76 (1H, s), 7.15–7.40 (10H, m), 7.65 (1H, d, J=8 Hz), 8.70 (1H, d, J=8 Hz), 9.18 (1H, s).

IR (KBr, cm$^{-1}$): 3310, 1802, 1748, 1687, 1660, 1555, 1532, 1367, 1242.

EXAMPLE 5

(3S,4S)-3-{N-benzyloxycarbonyl-β-(3-pyridyl)-L-alanyl}-amino-4-acetoxy-azetidin-2-one (5)

By a similar method as described in example 2, the title compound was obtained by reacting N-benzyloxycarbonyl-β-(3-pyridyl)-L-alanine with (3S,4S)-3-amino-4-acetoxy-azetidin-2-one.

Yield: 75%.
m.p.: 186° C. (dec.)
FAB-MS: 427 (MH$^+$), calcd for $C_{21}H_{22}N_4O_6$ 426
$^1$H NMR (DMSO-d$_6$), δ (ppm): 2.09 (3H, s), 2.75–3.15 (2H, m), 4.28 (1H, m), 4.66 (1 H, d, J=8.3 Hz), 4.94 (2H, m), 5.75 (1 H, s), 7.15–7.40 (6H, m), 7.65–7.75 (2H, m), 8.40–8.55 (2H, m), 8.85 (1H, d, J=8 Hz), 9.21 (1H, s).
IR(KBr,cm$^{-1}$): 3300, 1792, 1743, 1690, 1662, 1534, 1373, 1227.

EXAMPLE 6

(3S,4S)-3-(N-benzyloxycarbonyl-β-(2-pyridyl)-L-alanyl)-amino-4-acetoxy-azetidin- 2-one (6)

By a similar method as described in example 2, the title compound was obtained by reacting N-benzyloxycarbonyl-β-(2-pyridyl)-L-alanine with (3S,4S)-3-amino-4-acetoxy-azetidin-2-one.

Yield: 19%.
m.p.: 115–117° C.
FAB-MS: 427 (MH$^+$), calcd for $C_{21}H_{22}N_4O_6$ 426
$^1$H NMR (CDCl$_3$), δ (ppm): 2.10 (3H, s), 3.28 (2H, m), 4.70 (2H, m), 5.08 (2H, s), 5.72 (1H, s), 6.63 (1H, m), 7.10–7.40 (8H, m), 7.55–7.65 (1H, m), 8.35–8.50 (2H, m).
IR(KBr, cm$^{-1}$): 3315, 1792, 1741, 1716, 1686, 1655, 1526, 1256, 1222.

EXAMPLE 7

(3S,4S)-3-(N-benzyloxycarbonyl-β-(2-thienyl)-DL-alanyl)-amino-4-acetoxy-azetidin-2-one (7)

By a similar method as described in example 2, the title compound was obtained by reacting N-benzyloxycarbonyl-β-(2-thienyl)-DL-alanine with (3S,4S)-3-amino-4-acetoxy-azetidin-2-one.

Yield: 61%.
m.p.: 68–69° C.
FAB-MS: 432 (MH$^+$), calcd for $C_{20}H_{21}N_3O_6S$ 431
$^1$H NMR (DMSO-d$_6$), δ (ppm): 2.09 (3H, s), 2.95–3.30 (2H, m), 4.21 (1H, m), 4.64 (0.5H, d, J=8 Hz), 4.68 (0.5H, d, J=8 Hz), 5.00 (2H, m), 5.68 (0.5H, s) 5.75 (0.5H, s), 6.85–6.95 (2H, m), 7.25–7.40 (6H, m), 7.68 (0.5H, d, J=8 Hz), 7.72 (0.5H, d, J=8 Hz), 8.86 (0.5H, d, J=8 Hz), 8.88 (0.5H, d, J=8 Hz), 9.21 (0.5H, s), 9.22 (0.5H, s).
IR (KBr, cm$^{-1}$): 3300, 1790, 1747, 1718, 1697, 1670, 1536, 1506, 1225.

EXAMPLE 8

(3S,4S)-3-(N-benzyloxycarbonyl-β-(2-naphthyl)-L-alanyl)-amino-4-acetoxy-azetidin-2-one (8)

By a similar method as described in example 2, the title compound was obtained by reacting N-benzyloxycarbonyl-β-(2-naphthyl)-L-alanine with (3S,4S)-3-amino-4-acetoxy-azetidin-2-one.

Yield: 61%.
m.p.: 172–173° C.
FAB-MS: 476 (MH$^+$), calcd for $C_{26}H_{25}N_3O_6$ 475
$^1$H NMR (DMSO-d$_6$), δ (ppm): 2.07 (3H, s), 2.85–3.25 (2H, m), 4.38 (1H, m), 4.63 (1H, d, J=8 Hz), 4.92 (2H, m), 5.76 (1H, s), 7.05–7.25 (5H, m), 7.40–7.55 (3H, m), 7.67 (1H, d, J=8.7 Hz), 7.75–7.95 (4H, m), 8.85 (1H, d, J=8 Hz), 9.21 (1H, s).
IR (KBr, cm$^{-1}$): 3370, 1800, 1773, 1688, 1661, 1527, 1262, 1218.

EXAMPLE 9

(3S,4S)-3-{N-benzyloxycarbonyl-β-(3-fluorophenyl)-L-alanyl}-amino-4-acetoxy-azetidin-2-one (9)

By a similar method as described in example 1, the title compound was obtained by reacting N-benzyloxycarbonyl-β-(3-fluorophenyl)-L-alanine with (3S,4S)-3-amino-4-acetoxy-azetidin-2-one.

Yield: 52%.
m.p.: 166–167° C.
FAB-MS: 444 (MH$^+$), calcd for $C_{22}H_{22}FN_3O_6$ 443
$^1$H NMR (DMSO-d$_6$), δ (ppm): 2.11 (3H, s), 2.75–3.15 (2H, m), 4.28 (1H, m), 4.67 (1H, d, J=8 Hz), 4.97 (2H, m), 5.78 (1H, s), 7.00–7.40 (9H, m), 7.65 (1H, d, J=8.7 Hz), 8.84 (1H, d, J=8 Hz), 9.22 (1H, s).
IR (KBr, cm$^{-1}$): 3310, 1789, 1747, 1698, 1668, 1528, 1371, 1250, 1225.

EXAMPLE 10

(3S,4S)-3-{N-benzyloxycarbonyl-β-(4-methoxyphenyl)-L-alanyl}-amino-4-acetoxy-azetidin-2-one (10)

By a similar method as described in example 1, the title compound was obtained by reacting N-benzyloxycarbonyl-β-(4-methoxyphenyl)-L-alanine with (3S ,4S)-3-amino-4-acetoxy-azetidin-2-one.

Yield: 28%.
m.p.: 112–113° C.
FAB-MS: 456 (MH$^+$), calcd for $C_{23}H_{25}N_3O_6$ 455
$^1$H NMR (CdCl$_3$), δ (ppm): 2.11 (3H, s), 3.02 (2H, d, J=6.4 Hz), 3.77 (3H, s), 4.42 (1H, m), 4.59 (1H, d, J=7.3 Hz), 5.06 (2H, s), 5.38 (1H, d, J=7 Hz), 5.77 (1H, s), 6.80 (4H, m), 7.09 (2H, d, J=8.5 Hz), 7.25–7.40 (5H, m).
IR(KBr,cm$^{-1}$): 3380, 1811, 1748, 1680, 1524, 1369, 1286, 1245.

EXAMPLE 11

(3S,4S)-3-{N-benzyloxycarbonyl-β-(2-naphthyl)-L-alanyl}-amino-4-phenoxy-azetidin-2-one (11)

To a solution of phenol (30 mg, 0.32 mmol) in acetone (2 ml) and 1 N NaOH (0.25 ml), (3S,4S)-3{N-benzyloxycarbonyl-β-(2-naphthyl)-L-alanyl}-amino-4-acetoxy-azetidin-2-one (95 mg, 0.2 mmol) in acetone (1 ml) and THF (2 ml) was added at 5° C. The mixture was stirred at 5° C. for 1 hr and then at room temperature for 1 hr. After removal of solvent, the residue was dissolved in ethyl acetate, washed with water, brine and dried over sodium sulfate. After removal of solvent, the residue was purified by silica gel column chromatography using ethyl acetate-hexane (1:2) as eluent and 45 mg of (3S,4S)-3-{N-benzyloxycarbonyl-β-(2-naphthyl)-L-alanyl}-amino-4-phenoxy-azetidin-2-one was obtained.

Yield: 44%.
m.p.: 205–206° C.
FAB-MS: 510 (MH$^+$), calcd for $C_{30}H_{27}N_3O_5$ 509
$^1$H NMR (DMSO-d$_6$), δ (ppm): 2.85–3.30 (2H, m), 4.38 (1H, m), 4.70 (1 H, d, J=8.2 Hz), 4.94 (2H, m), 5.55 (1H, s), 6.85 –7.90 (18H, m), 8.99 (1H, d, J=8.3 Hz), 9.34 (1 H, s).
IR(KBr, cm$^{-1}$): 3280, 1798, 1681, 1654, 1525, 1489, 1351, 1298, 1229.

EXAMPLE 12

(3S,4S)-3{N-benzyloxycarbonyl-β-(2-naphthyl)-L-alanyl}-amino-4-(3-methyl phenoxy)-azetidin-2-one (12A) and (3S,4R)-3-{N-benzyloxycarbonyl-β-(2-naphthyl)-L-alanyl}-amino-4-(3-methylphenoxy)-azetidin-2-one (12B)

By a similar method as described in example 11, the title compounds (12A) and (12B) were obtained by reacting (3S,4S)-3-{N-benzyloxycarbonyl-β-(2-naphthyl)-L-alanyl}-amino-4-acetoxy-azetidin-2-one with 3-methylphenol.

For (12A):
Yield: 29%.
m.p.: 108.5 –109.5° C.
FAB-MS: 524 (MH$^+$), calcd for $C_{31}H_{29}N_3O_5$ 523
$^1$H NMR (DMSO-d$_6$), δ (ppm): 2.27 (3H, s), 2.90–3.30 (2H, m), 4.35–4.45 (1H, m), 4.67 (1H, d, J=8.3 Hz), 4.92 (2H, m), 5.53 (1H, s), 6.69 (2H, m), 6.84 (1H, d, J=7.4Hz), 7.10–7.25 (6H, m), 7.40–7.50 (3H, m), 7.70–7.90 (5H, m), 8.97 (1, d, J=8.3 Hz), 9.32 (1 H, s).
IR (KBr, cm–1): 3265, 1793, 1682, 1652, 1588, 1526, 1354, 1278, 1249.

For (12B):
Yield: 16%.
m.p.: 216–218° C.
FAB-MS: 524 (MH$^+$), calcd for $C_{31}H_{29}N_3O_5$ 523
$^1$H NMR (DMSO-d$_6$), δ (ppm): 2.25 (3H, s), 2.75–3.20 (2H, m), 4.40–4.50 (1H, m), 4.86 (2H, s), 5.42 (1H, m), 5.73 (1H, d, J=3.8 Hz), 6.70–6.85 (3H, m), 7.10–7.25 (6H, m), 7.40–7.60 (4H, m), 7.75–7.90 (4H, m), 8.95 (1H, d, J=9.2 Hz), 9.31 (1H, s).
IR (KBr, cm$^{-1}$): 3285, 1780, 1663, 1588, 1537, 1251.

EXAMPLE 13

(3S,4S)-3-{N-benzyloxycarbonyl-β-(2-naphthyl)-L-alanyl}amino-4-(2-naphthoxy)-azetidin-2-one (13A) and (3S,4R)-3-{N-benzyloxycarbonyl-β-(2-naphthyl)-L-alanyl}-amino-4-(2-naphthoxy)-azetidin-2-one (1 3B)

By a similar method as described in example 11, the title compounds (13A) and (13B) were obtained by reacting (3S,4S)-3-{N-benzyloxycarbonyl-β-(2-naphthyl)-L-alanyl}-amino-4-acetoxy-azetidin-2-one with 2-naphthol.

For (13A):
Yield: 13%.
m.p.: 224–225° C.
FAB-MS: 560 (MH$^+$), calcd for $C_{34}H_{29}N_3O_5$ 559
$^1$H NMR (DMSO-d$_6$), δ (ppm): 3.0–3.4 (2H, m), 4.45–4.55 (1 H, m), 4.77 (1 H, d, J=8.4 Hz), 4.97 (2H, m), 5.71 (1H, s), 7.15–7.30 (7H, m), 7.40–7.60 (5H, m), 7.80–7.95 (8H, m), 9.11 (1H, d, J=8.4 Hz), 9.43 (1H, s).
IR (KBr, cm$^{-1}$): 3305, 1792, 1649, 1535, 1372, 1275.

For (13B):
Yield: 13%.
m.p.: 109–110° C.
FAB-MS: 560 (MH$^+$), calcd for $C_{34}H_{29}N_3O_5$ 559
$^1$H NMR (DMSO-d$_6$), δ (ppm): 2.75–3.10 (2H, m), 4.35–4.50 (1H, m), 4.78 (2H, m), 5.45–5.55 (1H, m), 5.92 (1H, d, J=3.7 Hz), 7.05–7.60 (13H, m), 7.70–7.90 (7H, m), 9.02 (1H, d, J=9.0), 9.43 (1H, s).
IR (KBr, cm$^{-1}$): 3290, 1788, 1665, 1529, 1358, 1249.

EXAMPLE 14

(3S,4S)-3-{N-benzyloxycarbonyl-β-(2-naphthyl)-L-alanyl}amino-4-{3-(morpholin-4-yl)-phenoxy}-azetidin-2-one (1 4A) and (3S,4R)-3-{N-benzyloxycarbonyl-β-(2-naphthyl)-L-alanyl}-amino-4-{3-(morpholin-4-yl)-phenoxy}-azetidin-2-one (14B)

By a similar method as described in example 11, the title compounds (14A) and (14B) were obtained by reacting (3S,4S)-3-{N-benzyloxycarbonyl-β-(2-naphthyl)-L-alanyl}-amino-4-acetoxy-azetidin-2-one with 3-(morpholin4-yl)-phenol.

For (14A):
Yield: 15%.
m.p.: 140° C. (dec.)
FAB-MS: 595 (MH$^+$), calcd for $C_{34}H_{34}N_4O_6$ 594
$^1$H NMR (DMSO-d$_6$), δ (ppm): 2.90–3.30 (6H, m), 3.70–3.80 (4H, m), 4.35–4.50 (1H, m), 4.70 (1H, d, J=8.1 Hz), 4.95 (2H, m), 5.57 (1 H, s), 6.36 (1H, m), 6.44 (1H, s), 6.67 (1H, m), 7.10–7.30 (6H, m), 7.45–7.55 (3H, m), 7.71 (1H, d, J=8.6 Hz), 7.80–7.95 (4H, m), 9.00 (1H, d, J=8.1 Hz), 9.35 (1H, s).
IR (KBr, cm$^{-1}$): 3265, 1791, 1653, 1601, 1528, 1490, 1250.

For (14B):
Yield: 24%.
m.p.: 147° C. (dec.)
FAB-MS: 595 (MH$^+$), calcd for $C_{34}H_{34}N_4O_6$ 594
$^1$H NMR (DMSO-d$_6$), δ (ppm): 2.80–3.00 (1 H, m), 3.07 (5H, m), 3.68 (4H, m), 4.40–4.60 (1H, m), 4.85 (2H, s), 5.40–5.50 (1H, m), 5.73 (1H, d, J=3.7 Hz), 6.40–6.55 (2H, m), 6.60–6.70 (1H, m), 7.10–7.30 (6H, m), 7.45–7.60 (4H, m), 7.80–7.95 (4H$_1$ m), 8.95 (1 H, d, J=9.4), 9.31 (1 H, s).
IR (KBr, cm$^{-1}$): 3285, 1780, 1682, 1661, 1593, 1532, 1487 1249.

EXAMPLE 15

(3S,4SR)-3-{N-(3-phenylpropionoyl)-β-(2-naphthyl)-L-alanyl}-amino-4-phenylthio-azetidin-2-one (15)

By a similar method as described in example 11, the title compound 15 was obtained by reacting (3S,4S)-3{N-(3-phenylpropionoyl)-β-(2-naphthyl)-L-alanyl}-amino-4-acetoxy-azetidin-2-one with thiophenol.

Yield: 67%.
m.p.: 189–191° C.
FAB-MS: 524 (MH$^+$), calcd for $C_{31}H_{29}N_3O_3S$ 523
$^1$H NMR (DMSO-d$_6$), δ (ppm): 2.25–2.40 (2H, m), 2.55–2.70 (2H, m), 2.85–3.00 (1H, m), 3.10–3.25 (1H, m), 4.56 (0.5H, m), 4.60–4.70 (0.5H, m), 4.70–4.90 (0.5H, m), 4.92 (0.5H, d, J=2.3), 5.28 (0.5H, d, J=4.6 Hz), 5.35–5.45 (0.5H, m), 6.95–7.20 (5H, m), 7.25–7.50 (8H, m), 7.65–7.90 (4H, m), 8.19 (1 H, m), 8.84 (0.5H, d, J=8.3 Hz), 9.02 (0.5H, s), 9.05 (0.5H, s), 9.06 (0.5H, d, J=8 Hz).
IR (KBr,cm$^{-1}$): 3265, 3035, 1784, 1634, 1524, 1437, 1350, 1259, 1224.

EXAMPLE 16

(3S,4SR)-3-{N-(3-phenylpropionoyl)-β-(2-naphthyl)-L-alanyl}-amino-4-phenylsulfonyl-azetidin-2-one (16)

A mixture of (3S,4SR)-3-{N-(3-phenylpropionoyl)-β-(2-naphthyl)-L-alanyl}-amino-4-phenylthio-azetidin-2-one (52 mg, 0.1 mmol) obtained in example 15, and KMnO$_4$ (24 mg, 0.15 mmol) in acetic acid (2 ml) and H$_2$O (0.5 ml) was stirred at 5° C. for 1 hr and then room temperature for 1 hr. One drop of H$_2$O$_2$ (30% aq) was added. The reaction mixture was partitioned between ethyl acetate and water, the organic layer was washed with water, saturated NaHCO$_3$, water, brine and dried over Na$_2$SO$_4$. After removal of the solvent, solid was washed with ether and 40 mg of the title compound was obtained.

Yield: 72%.
m.p.: 175° C. (dec.)
FAB-MS: 556 (MH$^+$), calcd for $C_{31}H_{29}N_3O_5S$ 555
$^1$H NMR (DMSO-d$_6$), δ (ppm): 2.25–2.40 (2H, m), 2.55–2.65 (2H, m), 2.80–3.00 (1H, m), 3.05–3.25 (1H, m), 4.55–4.70 (0.5H, m), 4.80–4.95 (1.5H, m), 5.26 (0.5H, d, J=4.6 Hz), 5.50–5.60 (0.5H, m), 7.00–7.20 (5H, m), 7.30–7.95 (12H, m), 8.17 (0.5H, d, J=8 Hz), 8.22 (0.5H, d, J=8 Hz), 8.93 (1H, d, J=8.8 Hz), 9.36 (0.5H, s), 9.47 (0.5H, s).

IR (KBr, cm$^{-1}$): 3275, 1780, 1639, 1519, 1300.

EXAMPLE 17

(3S,4SR)-3-{N-(3-phenylpropionoyl)-β-(2-naphthyl)-L-alanyl}-amino-4-(2-hydroxyethylthio)-azetidin-2-one (17)

By a similar method as described in example 11, the title compound 17 was obtained by reacting (3S,4S)-3{N-(3-phenylpropionoyl)-β-(2-naphthyl)-L-alanyl}-amino-4-acetoxy-azetidin-2-one with 2-mercaptoethanol.

Yield: 26%.

m.p.: 134–136° C.

FAB-MS: 492 (MH$^+$), calcd for $C_{27}H_{29}N_3O_4S$ 491

$^1$H NMR (DMSO-d$_6$), δ (ppm): 2.30–2.40 (2H, m), 2.55–2.70 (4H, m), 2.85–3.00 (1H, m), 3.10–3.25 (1H, m), 3.45–3.60 (2H, m), 4.51 (0.6H, m), 5.70–5.80 (0.4H, m), 4.60–4.65 (1 H, m), 4.70 (0.6H, d, J=2.3 Hz), 5.00 (0.4H, d, J=4.5 Hz), 7.00–7.20 (5H, m), 7.35–7.50 (3H, m), 7.70–7.90 (4H, m), 8.15–8.25 (1H, m), 8.70–8.90 (2H, m).

IR (KBr, cm$^{-1}$): 3270, 1757, 1636, 1527.

EXAMPLE 18

(3S,4SR)-3{N-(3-phenylpropionoyl)-β-(2-naphthyl)-L-alanyl}-amino-4-benzyloxy-azetidin-2-one (18)

A mixture of (3S,4S)-3{N-(3-phenylpropionoyl)-β-(2-naphthyl)-L-alanyl}-amino-4-acetoxy-azetidin-2-one (236 mg, 0.5 mmol), benzyl alcohol (54 mg, 0.5 mmol), and zinc acetate dihydrate (110 mg, 0.5 mmol) in benzene (20 ml) and toluene (20 ml) was refluxed for 5 hrs using Dean-Stark water separator. After cooling, the reaction mixture was partitioned between ethyl acetate, containing a small volume of acetone, and water. The organic layer was washed with water, brine and dried over sodium sulfate. After removal of solvent, the residue was purified by silica gel column chromatography using hexane-ethyl acetate (1:1) as eluent and the title compound was obtained.

Yield: 23%.

m.p.: 171–172° C.

FAB-MS: 522 (MH$^+$), calcd for $C_{32}H_{31}N_3O_4$ 521

$^1$H NMR (CDCl$_3$), δ (ppm): 2.30–2.50 (2H, m), 2.65–2.85 (2H, m), 3.00–3.35 (2H, m), 4.40–4.55 (2.5H, m), 4.70–4.85 (1H, m), 5.01 (0.5H, s), 5.12 (0.5H, d, J=4.5 Hz), 5.20–5.30 (0.5H, m), 7.00–7.80 (18H, m), 8.20–8.30 (1H, m), 8.46 (0.5H, s), 8.61 (0.5H, s).

IR (KBr, cm$^{-1}$): 3265, 1767, 1635, 1531.

EXAMPLE 19

(3S,4SR)-3{N-(3-phenylpropionoyl)-β-(2-naphthyl)-L-alanyl}-amino-4-cyclohexyloxy-azetidin-2-one (19)

By a similar method as described in example 18, the title compound 19 was obtained by reacting (3S,4S)-3{N-(3-phenylpropionoyl)-β-(2-naphthyl)-L-alanyl}-amino-4-acetoxy-azetidin-2-one with cyclohexanol.

Yield: 35%.

m.p.: 169–171° C.

FAB-MS: 514 (MH$^+$), calcd for $C_{31}H_3N_3O_4$ 513

$^1$H NMR (CDCl$_3$), δ (ppm): 1.10–2.10 (1 OH, m), 2.40–2.55 (2H, m), 2.80–2.95 (2H, m), 3.05–3.40 (2H, m), 3.95–4.10 (1 H, m), 5.70–5.85 (1H, m), 6.31 (1H, m), 6.51 (1H, d, J=8.1 Hz), 7.10–7.90 (13H, m), 8.35 (1H, s), 8.64 (1H, s).

IR (KBr, cm$^{-1}$): 3275, 1780, 1639, 1519, 1300.

EXAMPLE 20

(3S,4S)-3-{N-(trans-2-phenyl-eth-1-enesulfonyl)-β-(2-naphthyl)-L-alanyl}-amino-4-acetoxy-azetidin-2-one (20)

(3S,4S)-3-{N-benzyloxycarbonyl-β-(2-naphthyl)-L-alanyl}-amino-4-acetoxy-azetidin-2-one (237 mg, 0.5 mmol) obtained in example 8, was hydrogenated with 400 mg of 10% palladium on activated carbon in ethyl acetate (20 ml) and THF (10 ml) at 50 psi hydrogen pressure at room temperature for 2 hrs. After removal of catalyst by filtration, the desubstituted (3S,4S)-3{β-(2-naphthyl)-L-alanyl}-amino-4-acetoxy-azetidin-2-one was cooled to –15° C. Then triethylamine (50 mg, 0.5 mmol) and trans-2-phenyl-eth-1-ene sulfonyl chloride (101 mg, 0.5 mmol) were added at –15° C. Stirring was continued at a bath temperature of –10 to 0° C. for 1 hr and 5° C. overnight. The reaction mixture was diluted with ethyl acetate, washed with cold saturated NaHCO$_3$ solution, water, brine and dried over sodium sulfate. After removal of solvent, the residue was purified by silica gel column chromatography using hexane-ethyl acetate (1:1) as eluent and the title compound (30 mg) was obtained.

Yield: 12%.

m.p.: 176° C. (dec.).

FAB-MS: 508 (MH$^+$), calcd for $C_{26}H_{25}N_3O_6S$ 507

$^1$H NMR (DMSO-d$_6$), δ (ppm): 2.01 (3H, s), 2.70–3.20 (2H, m), 4.05–4.20 (1H, m), 4.57 (1H, d, J=7.8 Hz), 5.61 (1H, s), 6.50 (1H, d, J=15.5 Hz), 7.14 (1H, d, J=15.5 Hz), 7.25–7.50 (8H, m), 7.70–7.85 (4H, m), 8.05 (1H, d, J=7.8 Hz), 8.90 (I H, d, J=7.9 Hz), 9.22 (1H, s).

IR (KBr, cm$^{-1}$): 3285, 1774, 1661, 1515, 1315, 1222.

EXAMPLE 21

(3S,4S)-3-{N-(benzylaminocarbonyl)-β-(2-naphthyl)-L-alanyl}-amino-4-acetoxy-azetidin-2-one (21)

By a similar method as described in example 2, the title compound was obtained by reacting N-(benzylaminocarbonyl)-β-(2-naphthyl)-L-alanine with (3S,4S)-3-amino-4-acetoxy-azetidin-2-one.

Yield: 70%.

m.p.: 203° C. (dec.).

FAB-MS: 475 (MH$^+$), calcd for $C_{26}H_{26}N_4O_5$ 474

$^1$H NMR (DMSO-d$_6$), δ (ppm): 2.05 (3H, s), 2.85–3.20 (2H, m), 4.05–4.20 (2H, m), 4.50–4.65 (1H, m), 4.57 (1 H, d, J=8.0 Hz), 5.73 (1 H, s), 6.22 (1 H, d, J=8.5 Hz), 6.55 (1 H, t, J=8.5 Hz), 7.05–7.20 (5H, m), 7.30–7.50 (3H, m), 7.65–7.90 (4H, m), 8.81 (1H, d, J=8.0 Hz), 9.17 (1H, s).

IR (KBr, cm$^{-1}$): 3325, 1799, 1744, 1652, 1626, 1555, 1222.

EXAMPLE 22

(3S,4SR)-3-{N-(benzylaminocarbonyl)-β-(2-naphthyl)-L-alanyl}-amino- 4-{4-(2S-2-amino-2-carboxy-ethyl)-phenoxy}-azetidin-2-one (22)

To a solution of 4-(2S-2-tert-butyloxycarbonylamino-2-diphenylmethoxy carbonyl-ethyl)-phenol (0.585 g, 1.3 mmol) in acetone (6 ml), H$_2$O (3 ml) and 1 N NaOH (1.2 ml), (3S,4S)-3-{N-(benzylaminocarbonyl)-β-(2-naphthyl)-L-alanyl}amino-4-acetoxy-azetidin-2-one (0.5 g, 1.09 mmol) in acetone (10 ml) and H$_2$O (5 ml) was slowly added at 5° C. The mixture was stirred at 5° C. for 2 hrs. After removal of solvent, the residue was dissolved in ethyl acetate, washed with water, brine and dried over sodium sulfate. After removal of solvent, the residue was recrystallized from ethyl acetate/hexane and 400 mg of (3S,4SR)-3-{N-(benzylaminocarbonyl)-β-(2-naphthyl)-L-alanyl}-amino-4-{(2S-2-tert-butyloxycarbonylamino-2-diphenylmethoxycarbonyl-ethyl)-phenoxy}-azetidin-2-one was obtained as white solid.

200 mg of (3S,4SR)-3{N-(benzylaminocarbonyl)-β-(2-naphthyl)-L-alanyl}-amino-4-{(2S-2-tertbutyloxycarbonylamino-2-diphenylmethoxycarbonyl-ethyl)-phenoxy}-azetidin-2-one was added to a mixture of anisole (1 ml), TFA (2 ml) and DCM (1 ml) at −15° C. The mixture was stirred at a bath temperature of −15 to 0° C. for 2 hrs. After removal of solvent, the resulting solid was washed with ether, ethyl acetate and acetonitril and 80 mg of the title compound was obtained as white solid.

Yield: 58%.
m.p.: 180° C. (dec.).
FAR-MS: 596 (MH$^+$), calcd for $C_{33}H_{33}N_5O_6$ 595
$^1$H NMR (DMSO-d$_6$), δ (ppm): 2.80–3.20 (4H, m), 3.65–3.80 (1H, m), 4.05–4.25 (2H, m), 4.50–4.65 (1 H, m), 4.65 (0.7H, d, J=8Hz), 5.50 (0.7H, s), 5.35–5.50 (0.3H, m), 5.75 (0.3H, d, J=3Hz), 6.20–6.35 (1H, m), 6.55–6.70 (1H, m 6.75–6.95 (2H, m), 7.05–7.25 (7H, m), 7.35–7.55 (3H, m), 7.70–7.90 (4H 8.90–9.00 (1 H, m), 9.33 (1 H, s).
IR (KBr, cm$^{-1}$): 3280, 3035, 1763, 1631, 1549, 1503, 1357, 1225.

EXAMPLE 23

(3S,4S)-3-{N-(3-phenylpropionyl)-L-citrullinyl}-amino-4-acetoxy-azetidin- 2-one (23)

By a similar method as described in example 2, the title compound was obtained by reacting N-(3-phenylpropionyl)-L-citrulline with (3S,4S)-3-amino-4-acetoxy-azetidin-2-one.

Yield: 35%.
m.p.: 193° C. (dec.).
FAB-MS: 434 (MH$^+$), calcd for $C_{20}H_{27}N_5O_6$ 433
$^1$H NMR (DMSO-d$_6$), δ (ppm): 1.20–1.70 (4H, m), 2.08 (3H, s), 2.40–2.50 (2H, m), 2.75–2.95 (4H, m), 4.20–4.35 (1H, m), 4.62 (1H, d, J=8.0 Hz), 5.37 (2H, s), 5.74 (1H, s), 5.89 (1H, m), 7.10–7.35 (5H, m), 8.08 (1H, d, J=8.0 Hz), 8.65 (1H, d, J=8.0 Hz), 9.18 (1H, s).
IR (KBr, cm$^{-1}$): 3290, 1793, 1738, 1652, 1541, 1363, 1323, 1216.

EXAMPLE 24

(3S,4S)-3-{N$^\alpha$-(3-phenylpropionyl)-N-nitro-L-arginyl}-amino-4-acetoxy-azetidin-2-one (24)

By a similar method as described in example 1, the title compound was obtained by reacting N$^\alpha$-(3-phenylpropionyl)-N$^\epsilon$-nitro-L-arginine with (3S,4S)-3-amino-4-acetoxy-azetidin-2-one.

Yield: 12%.
m.p.: 92° C. (dec.).
FAB-MS: 478 (MH$^+$), calcd for $C_{20}H_{27}N_4O_7$ 477
$^1$H NMR (DMSO-d$_6$), δ (ppm): 1.30–1.75 (4H, m), 2.08 (3H, s), 2.40–2.50 (2H, m), 2.75–2.95 (2H, m), 3.05–3.20 (2H, m), 4.20–4.35 (1 H, m), 4.62 (1H, d, J=8.2 Hz), 5.74 (1 H, s), 7.15–7.35 (5H, m), 7.70–8.20 (1 H, br), 8.08 (1H, d, J=8.1 Hz), 8.30–8.60 (1H, br), 8.66 (1H, d, J=8.2 Hz), 9.19 (1H, s).
IR (KBr, cm$^{-1}$): 3285, 1772, 1637, 1524, 1366, 1253.

EXAMPLE 25

(3S,4R)-3-(2S-2-benzyloxycarbonylamino-2-t-butyloxymethyl-acetamido)-4-phenoxy-azetidin-2-one (25)

To a solution of phenol (2.82 g 30 mmole) in THF (30 ml) and 1N NaOH (26 ml, 26 mmole), (3S, 4S)-3-benzyloxycarbonylamino-4-acetoxy-azetidin-2-one (5.56 g, 20 mmole) in THF (40 ml) and H$_2$O (20 ml) is added at 0° C. The mixture is stirred at 0° C for 1 hour and then at room temperature for 30 min. After removal of solvent, the residue is dissolved in ethyl acetate, washed with water, brine and dried over sodium sulphate. After removal of solvent, the residue is purified by silica gel column chromatography using hexane-ethyl acetate as eluent. 2.75 g of (3S, 4S)-3-benzyloxycarbonylamino-4-phenoxy-azetidin-2-one (A), 890 mg of (3S, 4R)-3-benzyloxycarbonylamino-4-phenoxy-azetidin-2-one (B) and 1.08 g of a mixture of (A) and (B) is obtained.

(3S, 4R)-3-benzyloxycarbonylamino-4-phenoxy-azetidin-2-one (1.85 g. 5.9 mmole) is hydrogenated with 2 g of 10% palladium on activated carbon in THF (30 ml) and ethyl acetate (30 ml) at 50 psi hydrogen pressure at room temperature for 2 hours. After removal of catalyst by filtration, 810 mg of deprotected (3S, 4R)-3-amino-4-phenoxy-azetidin-2-one is obtained.

To a solution of 2S-2-benzyloxycarbonylamino-2-t-butyloxymethyl-acetic acid (148 mg, 0.5 mmole), (3S, 4R)-3-amino-4-phenoxy-azetidin-2-one (80 mg, 0.45 mmole) in DMF (3 ml), BOP (221 mg, 0.5 mmole) and triethyl amine (101 mg, 1 mmole) is added. The reaction mixture is stirred at room temperature overnight and then diluted with ethyl acetate (50 ml) and ether (50 ml), washed with saturated NaHCO$_3$ solution, water, brine and dried over sodium sulfate. After removal of solvent, the residue is purified by silica gel column chromatography using hexane-ethyl acetate as eluent and 70 mg of the title compound is obtained.

Yield: 34%
m.p.: 135–136.5° C.
$^1$H-NMR (DMSO-d$_6$), δ (ppm): 1.05 (9H, s), 3.25–3.40 (2H, m), 4.05–4.20 (1H,m), 5.01 (2H,s), 5.33 (1H,m), 5.73 (1H,d,J=3.8 Hz), 6.85–7.10 (3H,m), 7.15 (1H,d, J=8.6 Hz), 7.20–7.40 (7H,m), 8.66 (1H, d, J=9.1 Hz), 9.27 (1H, s).

EXAMPLE 26

(3S, 4R)-3-[2S-2-benzyloxycarbonylamino-2-(1-t-butyloxyethyl)-acetamido]- 4-phenoxy-azetidin-2-one (26)

By a similar method as described in example 25, the title compound is obtained by reacting 2S-2-benzyloxycarbonylamino-2-(1-t-butyloxyethyl)-acetic acid and (3S, 4R)-3-amino-4-phenoxy-azetidin-2-one Yield: 57%
m.p.: 62–64° C.
$^1$H-NMR (DMSO-d$_6$),δ (ppm): 0.86 (3H, d, J=6 Hz), 0.98 (9H, s), 3.75–3.90 (1H,m), 3.95–4.10 (1H, m), 5.03 (2H,s), 5.39 (1H, m), 5.78 (1H, d, J=3.8 Hz), 6.80–7.10 (4H, m), 7.20–7.45 (7H,m), 8.53 (1H, d, J=9.4 Hz), 9.31 (1H, s).

EXAMPLE 27

(3S, 4S)-3-(2S-2-benzyloxycarbonylamino-2-t-butylmethyl-acetamido)-4-phenoxy-azetidin-2-one (27)

By a similar method as described in example 25, the title compound is obtained by reacting 2S-2-benzyloxycarbonylamino-2-t-butylmethyl-acetic acid and (3S, 4S)-3-amino-4-phenoxy-azetidin-2-one.

Yield: 71%
m.p.: 157–158° C.
$^1$H-NMR (DMSO-d$_6$),δ (ppm): 0.90 (9H,s), 1.50–1.80 (2H,m), 4.00–4.13 (1H, m), 4.66 (1H, d, J=8.4 Hz), 5.07 (2H, AB system, J=8.2 and 12.6 Hz), 5.54 (1H, s), 6.85–7.35 (10H,m), 7.56 (1H, d, J=8.2 Hz), 8.80 (1H, d, J=8.5 Hz), 9.30 (1H, s).

EXAMPLE 28

(3S, 4S)-3-[2S-2-(3-phenylpropionoyl)amino-2-t-butylmethyl-acetamido]-4-phenoxy-azetidin-2-one (28)

By a similar method as described in example 25, the title compound is obtained by reacting 2S-2-(3-phenylpropionoyl) amino-2-t-butylmethyl-acetic acid and (3S,4S)-3-amino-4-phenoxy-azetidin-2-one.

Yield: 68% m.p.: 169–171° C.

$^1$H-NMR (DMSO-d$_6$),δ (ppm): 0.86 (9H,s), 1.40–1.69 (2H,m), 2.40–2.50 (2H, m), 2.82 (2H, t, J=6.4 and 8.6 Hz), 4.27–4.39 (1 H, m), 4.63 (1 H, d, J=8.3 Hz), 5.54 (1H, s), 6.88–7.37 (10H, m), 8.13 (1H,d, J=8.1 Hz), 8.73 (1H, d, J=8.4 Hz), 9.29 (1 H,s).

EXAMPLE 29

(3S, 4S)-3-[2S-2-(3-phenylpropionoyl)amino-2-t-butyl-acetamido]-4-phenoxy-azetidin-2-one (29)

By a similar method as described in example 25, the title compound is obtained by reacting 2S-2-(3-phenylpropionoyl)amino-2-t-butyl-acetic acid and (3S, 4S)-3-amino-4-phenoxy-azetidin-2-one.

Yield: 43% m.p.: 104–105° C.

$^1$H-NMR (DMSO-d$_6$),δ (ppm): 0.89 (9H, s), 2.40–2.70 (2H,m), 2.82 (1H, t, J=8.2, 7.6 Hz), 4.22 (1H, d, J=9.1 Hz), 4.67 (1H,d, J=8.2 Hz), 5.55 (1H, s), 6.89–7.35 (10 H, m), 7.91 (1H, d, J=9 Hz), 8.85 (1H,d, J=8.4 Hz), 9.30 (1H, s).

EXAMPLE 30

(3S, 4s)-3-[2S-2-(3-phenylpropionoyl) amino-2-(3,4-dimethoxyphenyl) methyl-acetamido]-4-phenoxy-azetidin-2-one (30)

A solution of L-3,4-dihydroxyphenylalanine (1.97g, 10 mmole) in 2N NaOH (10 ml) is cooled in an ice-water bath. Hydrocinnamoyl chloride (1.8 g, 10.6 mmole) in THF (2 ml) and 1 N NaOH (10 ml) are added alternatingly at 0° C. The mixture is stirred at 0° C. for 1 hour and then room temperature for 1 hour. The alkaline solution is washed two times with ether. The aqueous layer is acidified to pH 2 and then extracted 3 times with ethyl acetate. The ethyl acetate layer is washed with brine and dried over sodium sulfate. After removal of solvent, the residue is dissolved in acetone (20 ml). Diazodiphenylmethane (1.63 g, 8.4 mmole) in acetone (20 ml) is added at 0° C. The reaction mixture is stirred at 0° C. for 2 hours and room temperature overnight. After removal of solvent, the residue is purified by silica gel column chromatography using hexane-ethyl acetate as eluent and 2.2 g of N-(3-phenylpropionoyl)-L-3,4-dihydroxyphenylalanine diphenylmethyl ester was obtained.

A reaction mixture of N-(3-phenylpropionoyl)-L-3,4-dihydroxyphenylalanine diphenylmethyl ester (248 mg, 0.5 mmole), CH$_3$I(213 mg, 1.5 mmole) and K$_2$CO$_3$(172 mg, 1.25 mmole) in acetone (10 ml) is stirred at room temperature overnight. After removal of solvent, the residue is dissolved in ethyl acetate, washed with water, brine and dried over sodium sulfate. After removal of solvent, the residue is purified by silica gel column chromatography using hexane-ethyl acetate as eluent and 160 mg of N-(3-phenylpropionoyl)-L-3,4-dimethoxyphenylalanine diphenylmethyl ester is obtained.

To a solution of N-(3-phenylpropionoyl)-L-3,4-dimethoxyphenylalanine diphenylmethyl ester (130 mg, 0.25 mmole) and anisole (0.5 ml) in dichloromethane (3 ml), trifluoroacetic acid (6 ml) is added at 0° C. The reaction mixture is stirred at 0° C. for 1 hour and room temperature for 30 min. The solution is evaporated to dryness in vacuo and the residue triturated with ether. After removal of solvent, 80 mg of 2S-2-(3-phenylpropionoyl) amino-2-(3,4-dimethoxyphenyl) methyl-acetic acid is obtained as white solid.

(3S, 4S)-3-benzyloxycarbonylamino-4-phenoxy-azetidin-2-one (63 mg, 0.2 mmole) is hydrogenated with 100 mg of 10% palladium on activated carbon in ethyl acetate (10 ml) at 50 psi hydrogen pressure at room temperature for 2 hours. After removal of catalyst by filtration, deprotected (3S, 4S)-3-amino-4-phenoxy-azetidin-2-one in ethyl acetate is obtained.

To a solution of 2S-2-(3-phenylpropionoyl) amino-2-(3, 4-dimethoxyphenyl) methyl-acetic acid (70 mg, 0.2 mmole) and 1-hydroxybenzotriazole (30 mg, 0.22 mmole) in THF (4 ml), DCC (41 mg, 0.2 mmole) is added. The reaction mixture is stirred at room temperature for 1 hour and then cooled with an ice bath. The resulting DCU is removed by filtration. Then a precooled solution of (3S, 4S)-3-amino-4-phenoxy-azetidin-2-one in ethyl acetate is added at 0° C. and the resulting mixture is stirred at 0° C. for 1 hour and room temperature for 1 hour. After removal of solvent, the residue is dissolved in ethyl acetate, washed with saturated NaHCO$_3$ solution, water, brine and dried over sodium sulfate. After removal of solvent, the residue is purified by recrystallization using hexane-ethyl acetate as solvent and 60 mg of title compound is obtained as white solid.

Yield: 58% m.p.: 183.5–185° C.

$^1$H-NMR (DMSO-d$_6$),δ (ppm): 2.35–2.45 (2H, m), 2.65–3.05 (4H,m), 3.65 (3H, s), 3.70 (3H,s), 4.45–4.60 (1 H, m), 4.64 (1 H, d, J=8.4 Hz), 5.51 (1 H, s 6.70–6.95 (3H,m), 7.00–7.40 (10 H, m), 8.19 (1H, d, J=8.1 Hz), 8.83 (1H,d, J=8.3 Hz), 9.32 (1H, s).

EXAMPLE 31

(3S, 4S)-3-[2S-3-phenylpropionoyl) amino-2-(3,4-ethylenedioxyphenylmethyl)-acetamido]-4-phenoxy-azetidin-2-one (31)

A reaction mixture of N-(3-phenylpropionoyl)-L-3,4-dihydroxyphenylalanine diphenylmethyl ester (360 mg, 0.72 mmole), 1-bromo-2-chloromethane (0.5 ml) and Cs$_2$CO$_3$ (472 mg, 1.45 mmole) in DMF (5 ml) is stirred at room temperature overnight and then at 90° C. for 1 hour. The reaction mixture is diluted with ethyl acetate and ether, and washed with water, brine and dried over sodium sulfate. After removal of solvent, the residue is purified by silica gel column chromatography using hexane-ethyl acetate as eluent and 240 mg of N-(3-phenylpropionoyl)-L-(3,4-ethylenedioxyphenyl)-alanine diphenylmethyl ester is obtained.

To a solution of N-(3-phenylpropionoyl)-L-(3,4-ethylenedioxyphenyl)-alanine diphenylmethyl ester (240 mg, 0.46 mmole) and anisole (0.5 ml) in dichloromethane (3 ml), trifluoroacetic acid (6 ml) is added at 0° C. The reaction mixture is stirred at 0° C. for 1 hour and room temperature for 30 min. The solution is evaporated to dryness in vacuo and the residue triturated with ether. After removal of solvent, 160 mg of 2S-2-(3-phenylpropionoyl)amino-2-(3, 4-ethylenedioxyphenylmethyl)-acetic acid is obtained as white solid.

(3S, 4S)-3-benzyloxycarbonylamino-4-phenoxy-azetidin-2-one (140 mg, 0.45 mmole) is hydrogenated with 100 mg of 10% palladium on activated carbon in ethyl acetate (20 ml) at 50 psi hydrogen pressure at room temperature for 2 hours. After removal of catalyst by filtration, deprotected (3S, 4S)-3-amino-4-phenoxy-azetidin-2-one in ethyl acetate is obtained.

To a solution of 2S-2-(3-phenylpropionoyl) amino-2-(3, 4-ethylenedioxyphenylmethyl)-acetic acid (160 mg, 0.45 mmole) and 1-hydroxybenzotriazole (66 mg, 0.49 mmole) in THF (6 ml), DCC (93 mg, 0.45 mmole) is added. The reaction mixture is stirred at room temperature for 1 hour and then cooled with an ice bath. The resulting DCU is removed by filtration. Then a precooled solution of (3S, 4S)-3-amino-4-phenoxy-azetidin-2-one in ethyl acetate is added at 0° C. and the resulting mixture is stirred at 0° C. for 1 hour and room temperature for 1 hour. After removal of solvent, the residue is dissolved in ethyl acetate, washed with saturated NaHCO$_3$ solution, water, brine and dried over sodium sulfate. After removal of solvent, the residue is purified by recrystallization using hexane-ethyl acetate as solvent and 140 mg of title compound is obtained as white solid.

Yield: 60% m.p.: 210–212° C.

$^1$H-NMR (DMSO-d$_6$), δ (ppm): 2.35–2.45 (2H, m), 2.60–3.00 (4H,m), 4.10–4.25 (4H, s), 4.40–4.55 (1H,m), 4.62 (1H, d, J=8.4 Hz), 5.51 (1H, s), 6.65–6.95 (3H,m), 7.00–7.40 (10 H, m), 8.19 (1H,d, J=8.1 Hz), 8.83 (1H, d, J=8.3 Hz); 9.32 (1 H, s).

EXAMPLE 32

(3S, 4S)-3-[2S-2-benzyloxycarbonylamino-2-(3-benzothienylmethyl)-acetamido]-4-phenoxy-azetidin-2-one (32)

By a similar method as described in example 25, the title compound is obtained by reacting 2S-2-benzyloxycarbonylamino-2-(3-benzothienylmethyl)-acetic acid and (3S, 4S)-3-amino-4-phenoxy-azetidin-2-one.

EXAMPLE 33

(3S, 4S)-3-[2S-2-benzyloxycarbonylamino-2-(4,4'-biphenylmethyl)-acetamido]- 4-phenoxy-azetidin-2-one (33)

By a similar method as described in example 25, the title compound is obtained by reacting 2S-2-benzyloxycarbonylamino-2-(4,4'-biphenylmethyl)-acetic acid and (3S, 4S)-3-amino-4-phenoxy-azetidin-2-one.

EXAMPLE 34

(3S, 4S)-3-[2S-2-benzyloxycarbonylamino-2-(2-chloro-phenylmethyl)-acetamido]4-phenoxy-azetidin-2-one (34)

By a similar method as described in example 25, the title compound is obtained by reacting 2S-2-benzyloxycarbonylamino-2-(2-chloro-phenylmethyl)-acetic acid and (3S, 4S)-3-amino-4-phenoxy-azetidin-2-one.

EXAMPLE 35

(3S, 4S)-3-[2S-2-benzyloxycarbonylamino-2-(4-chloro-phenylmethyl)-acetamido]-4-phenoxy-azetidin-2-one (35)

By a similar method as described in example 25, the title compound is obtained by reacting 2S-2-benzyloxycarbonylamino-2-(4-chloro-phenylmethyl)-acetic acid and (3S, 4S)-3-amino-4-phenoxy-azetidin-2-one.

EXAMPLE 36

(3S, 4S)-3-[2S-2-benzyloxycarbonylamino-2-(3,4-dichloro-phenylmethyl)-acetamido]-4-phenoxy-azetidin-2-one (36)

By a similar method as described in example 25, the title compound is obtained by reacting 2S-2-benzyloxycarbonylamino-2-(3,4-dichloro-phenylmethyl)-acetic acid and (3S, 4S)-3-amino-4-phenoxy-azetidin-2-one.

EXAMPLE 37

(3S, 4S)-3-[2S-2-benzyloxycarbonylamino-2-(diphenylmethyl)-acetamido]-4-phenoxy-azetidin-2-one (37)

By a similar method as described in example 25, the title compound is obtained by reacting 2S-2-benzyloxycarbonylamino-2-(diphenylmethyl)-acetic acid and (3S, 4S)-3-amino-4-phenoxy-azetidin-2-one.

EXAMPLE 38

(3S, 4S)-3-[2S-2-benzyloxycarbonylamino-2-(2-fluoro-phenylmethyl)-acetamido]- 4-phenoxy-azetidin-2-one (38)

By a similar method as described in example 25, the title compound is obtained by reacting 2S-2-benzyloxycarbonylamino-2-(2-fluoro-phenylmethyl)-acetic acid and (3S, 4S)-3-amino-4-phenoxy-azetidin-2-one.

EXAMPLE 39

(3S, 4S)-3-[2S-2-benzyloxycarbonylamino-2-(4-fluoro-phenylmethyl)-acetamido]-4-phenoxy-azetidin-2-one (39)

By a similar method as described in example 25, the title compound is obtained by reacting 2S-2-benzyloxycarbonylamino-2-(4-fluoro-phenylmethyl)-acetic acid and (3S, 4S)-3-amino-4-phenoxy-azetidin-2-one.

EXAMPLE 40

(3S, 4S)-3-[2S-2-benzyloxycarbonylamino-2-(3,4-difluoro-phenylmethyl)-acetamido]-4-phenoxy-azetidin-2-one (40)

By a similar method as described in example 25, the title compound is obtained by reacting 2S-2-benzyloxycarbonylamino-2-(3,4-difluoro-phenylmethyl)-acetic acid and (3S, 4S)-3-amino-4-phenoxy-azetidin-2-one.

EXAMPLE 41

(3S, 4S)-3-[2S-2-benzyloxycarbonylamino-2-(4-iodo-phenylmethyl)-acetamido]-4-phenoxy-azetidin-2-one (41)

By a similar method as described in example 25, the title compound is obtained by reacting 2S-2-benzyloxycarbonylamino-2-(4-iodo-phenylmethyl)-acetic acid and (3S, 4S)-3-amino-4-phenoxy-azetidin-2-one.

EXAMPLE 42

(3S, 4S)-3-[2S-2-benzyloxycarbonylamino-2-(naphth-1-yl) methyl-acetamido]-4-phenoxy-azetidin-2-one (42)

By a similar method as described in example 25, the title compound is obtained by reacting 2S-2-benzyloxycarbonylamino-2-(naphth-1-yl)methyl-acetic acid and (3S, 4S)-3-amino-4-phenoxy-azetidin-2-one.

EXAMPLE 43

(3S, 4S)-3-[2S-2-benzyloxycarbonylamino-2-(4-nitro-phenylmethyl)-acetamido]- 4-phenoxy-azetidin-2-one (43)

By a similar method as described in example 25, the title compound is obtained by reacting 2S-2-benzyloxycarbonylamino-2-(4-nitro-phenylmethyl)-acetic acid and (3S, 4S)-3-amino-4-phenoxy-azetidin-2-one.

EXAMPLE 44

(3S, 4S)-3-[2S-2-benzyloxycarbonylamino-2-(pentafluorophenyl-methyl)-acetamido]4-phenoxy-azetidin-2-one (44)

By a similar method as described in example 25, the title compound is obtained by reacting 2S-2-benzyloxycarbonylamino-2-(pentafluorophenyl-methyl)-acetic acid and (3S, 4S)-3-amino-4-phenoxy-azetidin-2-one.

EXAMPLE 45

(3S, 4S)-3-[2S-2-benzyloxycarbonylamino-2-(4-thiazolylmethyl)-acetamido]-4-phenoxy-azetidin-2-one (45)

By a similar method as described in example 25, the title compound is obtained by reacting 2S-2-benzyloxycarbonylamino-2-(4-thiazolylmethyl)-acetic acid and (3S, 4S)-3-amino-4-phenoxy-azetidin-2-one.

EXAMPLE 46

(3S, 4S)-3-[2S-2-benzyloxycarbonylamino-2-(3-trifluoromethylphenyl-methyl)-acetamido]-4-phenoxy-azetidin-2-one (46)

By a similar method as described in example 25, the title compound is obtained by reacting 2S-2-benzyloxycarbonylamino-2-(3-trifluoromethylphenyl methyl)-acetic acid and (3S, 4S)-3-amino-4-phenoxy-azetidin-2-one.

EXAMPLE 47

(3S, 4S)-3-[2S-2-benzyloxycarbonylamino-2-(3-sulfamoylmethyl)-acetamido]-4-phenoxy-azetidin-2-one (47)

By a similar method as described in example 25, the title compound is obtained by reacting 2S-2-benzyloxycarbonylamino-2-(3-sulfamoylmethyl)-acetic acid and (3S, 4S)-3-amino-4-phenoxy-azetidin-2-one.

EXAMPLE 48

(3S, 4S)-3-[2S-2-(3-phenylpropionoyl) amino-2-(3,4-methylenedioxyphenylmethyl)-acetamido]-4-phenoxy-azetidin-2-one (48)

By a similar method as described in example 30, the title compound is obtained by reacting 2S-2-(3-phenylpropionoyl) amino-2-(3,4-methylenedioxyphenyl) methyl acetic acid and (3S, 4S)-3-amino-4-phenoxy-azetidin-2-one.

EXAMPLE 49

(3S, 4S)-3-[2S-2-(3-phenylpropionoyl) amino-2-(3,4-diisopropyloxyphenylmethyl)-acetamido]-4-phenoxy-azetidin-2-one (49)

By a similar method as described in example 30, the title compound is obtained by reacting 2S-2-(3-phenylpropionoyl) amino-2-(3,4-diisopropyloxyphenyl) methyl acetic acid and (3S, 4S)-3-amino-4-phenoxy-azetidin-2-one.

EXAMPLE 50

(3S, 4S)-3-[2S-2-benzyloxycarbonylamino-2-butyl-acetamido]-4-phenoxy-azetidin-2-one (50)

By a similar method as described in example 25, the title compound is obtained by reacting 2S-2-benzyloxycarbonylamino-2-butyl-acetic acid and (3S, 4S)-3-amino-4-phenoxy-azetidin-2-one.

EXAMPLE 51

(3S, 4S)-3-[2S-2-benzyloxycarbonylamino-2-propyl-acetamido]-4-phenoxy-azetidin-2-one (51)

By a similar method as described in example 25, the title compound is obtained by reacting 2S-2-benzyloxycarbonylamino-2-propyl-acetic acid and (3S, 4S)-3-amino-4-phenoxy-azetidin-2-one.

Testing of Inhibitors for Inhibition of Cathepsin B and L

TEST EXAMPLE 1

In vitro assay procedure for cathepsin B

The compounds of formula I were tested for inhibition of cathepsin B using the known method (A. J. Barret et al., Biochem. J. 1982, 201, 189–198). To a 170 μl of enzyme-buffer mixture (enzyme: r rat cathepsin B, diluted to give approximate 10 F units/min, buffer: 56 mM sodium acetate, 1.124 mM EDTA, 10 mM DTT, pH 5.1) a 10 μL of inhibitor (dissolved in DMSO) was added. After 10 min of incubation at room temperature, a 20 μl of 5 mM substrate (N-CBZ-Phe-Arg-AMC, dissolved in DMSO) was added to initiate reaction. Reading is followed up for 10 min at the fluoroscan reader (excitation at 380 nm emission at 460 nm).

A plot of percentage of inhibition vs inhibitor concentration is obtained, and $IC_{50}$ is determined using a linear regression calculation (concentration of inhibitor which will give 50% inhibition).

TEST EXAMPLE 2

In vitro assay procedure for cathepsin L

To a 170 μl of enzyme-buffer mixture (enzyme: r rat cathepsin L, diluted to give approximate 15 F units/min, buffer: 58.8 mM sodium citrate, 1.18 mM EDTA, 235 mM sodium chloride, 5 mM DTT, pH 5.0) a 10 μL of inhibitor (dissolved in DMSO) was added. After 10 min of incubation at room temperature, a 20 μl of 1 mM substrate (N-CBZ-Phe-Arg-AMC, dissolved in DMSO) was added to initiate reaction. Reading is followed up for 10 min at the fluoroscan reader (excitation at 380 nm emission at 460 nm).

A plot of percentage of inhibition vs inhibitor concentration is obtained, and $IC_{50}$ is determined using a linear regression calculation (concentration of inhibitor which will give 50% inhibition).

TABLE 1

In vitro inhibitory activity of monobactam compounds on cysteine proteases

| Example No. | $IC_{50}$ (μM) Cathepsin B | Cathepsin L |
|---|---|---|
| 1 | >50 | 26.7 |
| 2 | >50 | >50 |
| 3 | >50 | 43.09 |
| 4 | >50 | 11.39 |
| 5 | >50 | 8.26 |
| 6 | >50 | 12.08 |
| 7 | 28.57 | 2.32 |
| 8 | 16.42 | 0.0135 |
| 9 | 18.85 | 0.341 |
| 10 | 7.51 | 0.057 |
| 11 | 0.9 | 0.015 |
| 12A | 0.38 | 0.003 |
| 12B | 0.08 | 0.0004 |
| 13A | 1.8 | 0.0029 |
| 13B | 0.0715 | 0.00011 |
| 14A | 1.7 | 0.0027 |
| 14B | 0.34 | 0.0005 |
| 15 | 1.91 | 0.0061 |
| 16 | 1.6 | 0.0086 |
| 17 | 10.1 | 0.4 |
| 18 | 1.92 | 0.0767 |
| 19 | 1.95 | 0.39 |
| 20 | 0.395 | 0.079 |
| 21 | 2.2 | 0.01 |
| 22 | 8.4 | 0.013 |
| 23 | 11.0 | 11.5 |
| 24 | 31.4 | 0.0168 |
| 25 | 11 | 2.19 |
| 26 | >50 | 10.65 |
| 27 | 23 | 2.3 |
| 28 | 45 | 11.43 |

TABLE 1-continued

In vitro inhibitory activity of monobactam compounds on cysteine proteases

| Example No. | IC$_{50}$ ($\mu$M) Cathepsin B | Cathepsin L |
|---|---|---|
| 29 | >50 | >50 |
| 30 | 48 | 1.6 |
| 31 | 9.7 | 0.08 |

Although the compounds and compositions, and methods of making and administering them in accordance with the present invention have been described in connection with preferred embodiments, it will be appreciated by those skilled in the art that modifications not specifically described may be made without departing from the spirit and scope of the invention defined in the following claims.

We claim:

1. A 3,4-disubstituted-azetidin-2-one compound of formula I, or a pharmaceutically acceptable salt thereof:

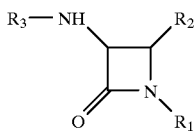

wherein

R$_1$ is hydrogen; or

—SO$_3^-$M$^+$ wherein M is a hydrogen atom, a metal ion which is selected from sodium, potassium, magnesium, and calcium, or N$^+$(R$_4$)$_4$ wherein R$_4$ is a C$_1$–C$_6$ alkyl group;

R$_2$ is (a) a group —OCOR$_5$ wherein R$_5$ is (i) a C$_1$–C$_6$ alkyl group, (ii) a C$_2$–C$_6$ alkenyl group, (iii) a C$_2$–C$_6$ alkynyl group, (iv) a C$_3$–C$_6$ cycloalkyl group, (v) a phenyl group, (vi) a naphthyl group, or (vii) a monocyclic or bicyclic heterocyclic group, which group (i), (ii), (iii), (iv), (v), (vi), or (vii) is unsubstituted or substituted by 1, 2 or 3 substituents independently selected from hydroxy, halogen, carboxy, C$_1$–C$_4$ alkyl (which is unsubstituted or substituted at least once with carboxy and/or amino), C$_1$–C$_2$ alkoxy, amino, cyano, and phenyl and monocyclic or bicyclic heterocyclic groups, which phenyl and heterocyclic groups are unsubstituted or substituted by 1 or 2 substituents independently selected from hydroxy, halogen, carboxy, C$_1$–C$_4$ alkyl, C$_1$–C$_2$ alkoxy, amino, and cyano;

or (b) a group —XR$_5$ wherein X is selected from the group consisting of O, S, SO, and SO$_2$, and R$_5$ is as defined above;

R$_3$ is selected from the group consisting of D- or L-t-butyl alanine, D- or L-homophenyl alanine, D- or L-pyridyl alanine, D- or L-thienyl alanine, D- or L-naphthyl alanine, D- or L-methoxy phenyl alanine, D- or L-halo phenyl alanine, D- or L-ε-nitro arginine, D- or L-citrulline, D- or L-4-hydroxy-3-nitro-phenylalanine, D- or L-4-amino-3,5-diiodo-phenylalanine, D- or L-4-hydroxy-3,5-diiodo-phenylalanine, D- or L-4-hydroxy-3,5-dibromo-phenylalanine, D- or L-β-(3-benzothienyl)-alanine, D- or L-3,4(methylenedioxy) phenylalanine, D- or L-3,4(ethylenedioxy) phenylalanine, D- or L-4, 4'-biphenylalanine, D- or L-3,4-dichlorophenylalanine, D- or L-4-iodophenylalanine, D- or L-4-nitrophenylalanine, D- or L-pentafluorophenylalanine, D- or L-4-thiazolylalanine, D- or L-3-trifluoromethylphenylalanine, D- or L-4-trifluoromethylphenylalanine, and D- or L-3,4-diisopropyloxyphenylalanine in which the NH$_2$ of any of the above groups is substituted once or twice with R$_7$, wherein R$_7$ is —COOR$_5$, —COR$_5$, —SO$_2$R$_5$, or —COR$_{14}$;

R$_5$ is as defined above; and

R$_{14}$ is an amino group which is unsubstituted or substituted at least once with a C$_1$–C$_6$ alkyl group which is unsubstituted or substituted at least once with 1 or 2 substituents selected from hydroxy, halogen, cyano, amino, heterocycle, and phenyl wherein said heterocycle or phenyl is unsubstituted or substituted at least once by 1 or 2 moieties selected from halogen, hydroxy, cyano, carboxy, and amino.

2. A compound or salt as recited in claim 1, wherein R$_1$ is selected from hydrogen and sulphonic acid.

3. A compound or salt as recited in claim 1, wherein R$_2$ is selected from acetoxy, butyloxy, 2-carboxy ethyloxy, 2-aminoethyloxy, 2-fluoro ethoxy, cyclopentyloxy, cyclohexyloxy, cyclohexylthio, phenoxy, methyl phenoxy, naphthyloxy, morpholino phenyloxy, 2-hydroxy ethylthio, phenylthio, phenylsulphonyl, 4-(2-carboxy-2-amino ethyl)-phenoxy, 4-carboxy phenoxy, 3-carboxy phenoxy, 2-pyridylthio, 4-pyridylthio, and benzyloxy.

4. A compound or salt as recited in claim 1, wherein R$_3$ is selected from the group consisting of N-benzyloxycarbonyl homophenyl alanine, N-benzyloxycarbonyl pyridyl alanine, N-benzyloxycarbonyl thienyl alanine, N-benzyloxycarbonyl naphthyl alanine, N-benzyloxycarbonyl halophenyl alanine, N-benzyloxycarbonyl naphthyl alanine, N-(3-phenyl propanoyl) naphthyl alanine, phenyl propionyl-N$^\epsilon$-nitro-arginine, N-(3-phenyl propanoyl) citrulline, N-benzylamino carbonyl naphthyl alanine, N-(2-phenyl-eth-1en-sulphonyl)-naphthyl alanine, N-phenylpropionoyl-(3,4-dimethoxyphenyl) alanine, N-phenylopropionoyl-(3,4-ethylenedioxyphenyl) alanine, N-benzyloxycarbonyl-3-benzothienyl alanine, N-benzyloxycarbonyl-(4, 4'-biphenyl) alanine, N-benzyloxycarbonyl-(2-chlorophenyl)alanine, N-benzyloxycarbonyl-(4-chlorophenyl)alanine, N-benzyloxycarbonyl-(3,4-dichloro)-phenylalanine, N-benzyloxycarbonyl-(2-fluoro) phenylalanine, N-benzyloxycarbonyl-(4-fluoro-phenyl) alanine, N-benzyloxycarbonyl-(3,4-difluoro-phenyl) alanine, N-benzyloxycarbonyl-(4-iodo-phenyl) alanine, N-benzyloxycarbonyl-2-(naphthyl) alanine,
N-benzyloxycarbonyl-(4-nitro-phenyl) alanine,
N-benzyloxycarbonyl-(pentafluorophenyl) alanine,
N-benzyloxycarbonyl-(4-thiazolyl) alanine,
N-benzyloxycarbonyl-3-(trifuloromethylphenyl) alanine,
N-benzyloxycarbonyl-4-trifluoromethylphenyl) alanine,
N-phenylpropionoyl-(3,4-methylenedioxyphenyl) alanine
and N-phenylpropionoyl-(3,4-diisopropyloxyphenyl) alanine.

5. A compound or salt as recited in claim 1, having (3R,4S), (3R,4R), (3S,4R) or (3S,4S) configuration at two asymmetric carbons 3 and 4 on azetidin-2-one ring system or a racemic mixture thereof.

6. A compound or salt as recited in claim 1, wherein said unnatural amino acid residue is a D isomer, an L isomer, or a racemic mixture thereof.

7. A compound or salt as recited in claim 1, wherein $R_7$ is selected from the group consisting of aryloxycarbonyl, alkoxycarbonyl, substituted alkanoyl, arylalkanoyl, arylalkenoyl, heterocyclealkenoyl, heterocyclealkanoyl, alkylsulphonyl, arylsulphonyl, arylalkanylsulphonyl, arylalkensulphonyl, heterocyclealkanylsulphonyl, heterocyclealkensulphonyl, and heterocyclesulphonyl.

8. A salt as recited in claim 1, wherein said salt is the salt of an acid selected from hydrogen chloride, tartaric acid, succinic acid, fumaric acid and p-toluenesulfonic acid, or said salt contains a metal cation selected from the group consisting of sodium, potassium, magnesium and calcium.

9. A 3,4-disubstituted-azetidin-2-one compound as recited in claim 1 having formula I, or a pharmaceutically acceptable salt thereof:

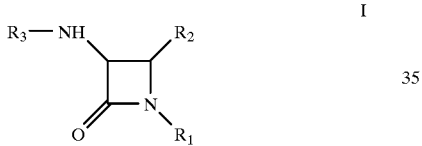

wherein
$R_1$ is
hydrogen; or
—$SO_3^- M^+$ wherein M is a hydrogen atom, a metal ion which is selected from sodium, potassium, magnesium, and calcium, or $N^+(R_4)_4$ wherein $R_4$ is a $C_1$–$C_6$ alkyl group;
$R_2$ is
—$OCOR_5$ wherein R, is (i) a $C_1$–$C_6$ alkyl group which is unsubstituted or substituted at least once by 1 or 2 substituents selected from hydroxy, halogen, and amino, or (ii) a phenyl group which is unsubstituted or substituted at least once by 1–3 substituents selected from hydroxy, halogen, $C_1$–$C_4$ alkyl group, $C_1$–$C_2$ alkoxy group, and cyano; or
—$XR_6$ wherein X is O, S, SO, or $SO_2$; $R_6$ is (i) a $C_1$–$C_6$ alkyl group which is unsubstituted or substituted at least once by 1 or 2 substituents selected from hydroxy, halogen, amino and phenyl (ii) a $C_3$–$C_6$ cycloalkyl group, (iii) a phenyl group which is unsubstituted or substituted at least once by 1–3 substituents selected from hydroxy, halogen, carboxyl, $C_1$–$C_4$ alkyl group (which is unsubstituted or substituted with carboxy, amino or both), $C_1$–$C_2$ alkoxy group, cyano and monocyclic or bicyclic heterocyclic groups, or (iv) naphthyl group which is unsubstituted or substituted at least once by 1–3 substituents selected from hydroxy, halogen, carboxy, $C_1$–$C_4$ alkyl group (which is unsubstituted or substituted at least once with carboxy, amino or both), $C_1$–$C_2$ alkoxy group and cyano;

$R_3$ is selected from the group consisting of D- or L-t-butyl alanine, D- or L-homophenyl alanine, D- or L-pyridyl alanine, D- or L-thienyl alanine, D- or L-naphtyl alanine, D- or L-methoxy phenyl alanine, D- or L-halo phenyl alanine, D- or L-ε-nitro arginine, D-or L-citrulline, D- or L-4-hydroxy-3-nitro-phenylalanine, D- or L-4-amino-3,5-diiodo-phenylalanine, D- or L-4-hydroxy-3,5-diiodo-phenylalanine, D- or L-4-hydroxy-3,5-dibromo-phenylalanine, D- or L-β-(3-benzothienyl)-alanine, D- or L-3,4(methylenedioxy) phenylalanine, D- or L-3,4(ethylenedioxy) phenylalanine, D- or L-4,4'-biphenylalanine, D- or L-3,4-dichlorophenylalaine, D- or L-4-iodophenylalanine, D- or L-4-nitrophenylalanine, D- or L-pentafluorophenylalanine, D- or L-4-thiazolylalanine, D- or L-3-trifluoromethylphenylalanine, D- or L-4-trifluoromethylphenylalanine, D-or L-3-sulfamoyl-alanine, and D- or L-3,4-diisopropyloxyphenylalanine, and alanine, in which the $NH_2$ of any of the above groups is substituted once or twice with $R_7$ wherein $R_7$ is
—$COOR_8$ wherein $R_8$ is a $C_1$–$C_6$ alkyl group which is unsubstituted or substituted at least once with phenyl group,
—COR, wherein $R_9$ is
(i) a $C_1$–$C_6$ alkyl group which is unsubstituted or substituted at least once by 1 or 2 substituents selected from hydroxy, halogen, cyano, amino, monocyclic or bicyclic heterocyclic groups or phenyl (wherein the heterocyclic groups or phenyl is unsubstituted or substituted at least once by 1 or 2 substituents selected from halogen, hydroxy, cyano, carboxy and amino); (ii) monocyclic or bicyclic heterocyclic group or (iii) amino group which is unsubstituted or substituted at least once with $C_1$–$C_6$ alkyl group which is unsubstituted or substituted at least once with 1 or 2 substituents selected from hydroxy, halogen, cyano, amino, heterocycle, and phenyl (wherein the heterocycle or phenyl is unsubstituted or substituted at least once by 1 or 2 substituents selected from halogen, hydroxy, cyano, carboxy and amino); or
$SO_2R_{10}$ wherein $R_{10}$ is
(i) a $C_1$–$C_6$ alkyl group (ii) a $C_2$–$C_4$ alkenyl group which is unsubstituted or substituted at least once with a monocyclic or bicyclic heterocyclic group or phenyl, or (iii) a phenyl group which is unsubstituted or substituted at least once by 1–3 substituents selected from hydroxy, halogen, carboxy, $C_1$–$C_4$ alkyl group, $C_1$–$C_2$ alkoxy group and cyano.

10. A compound selected from the group consisting of:
(3S,4S)-3-(N-benzyloxycarbonyl-L-homophenylalanyl)-amino-4-acetoxy-azetidin-2-one;
(3S,4S)-3-{N-benzyloxycarbonyl-β-(3-pyridyl)-L-alanyl}-amino-4-acetoxy-azetidin-2-one;
(3S,4S)-3-{N-benzyloxycarbonyl-β-(2-pyridyl)-L-alanyl}-amino-4-acetoxy-azetidin-2-one;
(3S,4S)-3-{N-benzyloxycarbonyl-β-(2-thienyl)-DL-alanyl}-amino-4-acetoxy-azetidin-2-one;
(3S,4S)-3-{N-benzyloxycarbonyl-β-(2-naphthyl)-L-alanyl}-amino-4-acetoxy-azetidin-2-one;

(3S,4S)-3-{N-benzyloxycarbonyl-β-(3-fluorophenyl)-L-alanyl}-amino-4-acetoxy-azetidin-2-one;

(3S,4S)-3-{N-benzyloxycarbonyl-β-(4-methoxyphenyl)-L-alanyl}-amino-4-acetoxy-azetidin-2-one;

(3S,4S)-3-{N-benzyloxycarbonyl-β-(2-naphthyl)-L-alanyl}-amino-4-phenoxy-azetidin-2-one;

(3S,4S)-3-{N-benzyloxycarbonyl-β-(2-naphthyl)-L-alanyl}amino-4-(3-methyl phenoxy)-azetidin-2-one;

(3S,4R)-3-{N-benzyloxycarbonyl-β-(2-naphthyl)-L-alanyl}-amino-4-(3-methyl phenoxy)-azetidin-2-one;

(3S,4S)-3-{N-benzyloxycarbonyl-β-(2-naphthyl)-L-alanyl}-amino-4-(2-naphthoxy)-azetidin-2-one;

(3S,4R)-3-{N-benzyloxycarbonyl-β-(2-naphthyl)-L-alanyl}-amino-4-(2-naphthoxy)-azetidin-2-one;

(3S,4S)-3-{N-benzyloxycarbonyl-β-(2-naphthyl)-L-alanyl}-amino-4-{3-(morpholin-4-yl)-phenoxy}-azetidin-2-one;

(3S,4R)-3-{N-benzyloxycarbonyl-β-(2-naphthyl)-L-alanyl}-amino-4-{3-(morpholin-4-yl)-phenoxy}-azetidin-2-one;

(3S,4SR)-3-{N-(3-phenylpropionoyl)-β-(2-naphthyl)-L-alanyl}-amino-4-phenylthio-azetidin-2-one;

(3S,4SR)-3-{N-(3-phenylpropionoyl)-β-(2-naphthyl)-L-alanyl}-amino-4-phenylsulphonyl-azetidin-2-one;

(3S,4SR)-3-{N-(3-phenylpropionoyl)-β-(2-naphthyl)-L-alanyl}-amino-4-(2-hydroxy ethyl thio)-azetidin-2-one;

(3S,4SR)-3-{N-(3-phenylpropionoyl)-β-(2-naphthyl)-L-alanyl}-amino-4-benzyloxy-azetidin-2-one;

(3S,4SR)-3-{N-(3-phenylpropionoyl)-β-(2-naphthyl)-L-alanyl}-amino-4-cyclohexyloxy-azetidin-2-one;

(3S,4S)-3-{N-(trans-2-phenyl-eth-1-enesulfonyl)-β-(2-naphthyl)-L-alanyl}-amino-4-acetoxy-azetidin-2-one;

(3S,4SR)-3-{N-(3-phenylpropionoyl)-β-(2-naphthyl)-L-alanyl}-amino-4-{4-(2S-2-amino-2-carboxyethyl)-phenoxy}-azetidin-2-one;

(3S,4S)-3-{N-(benzylaminocarbonyl)-β-(2-naphthyl)-L-alanyl}-amino-4-acetoxy-azetidin-2-one;

(3S,4SR)-3-{N-(benzylaminocarbonyl)-β-(2-naphthyl)-L-alanyl}-amino-4-{4-(2S-2-amino-2-carboxyethyl)-phenoxy}-azetidin-2-one;

(3S,4S)-3-{N-(3-phenylpropionoyl)-L-citrullinyl}-amino-4-acetoxy-azetidin-2-one;

(3S,4S)-3-{N-(2-phenyl-eth-1-en-sulphonyl)-β-(2-naphthyl)-L-alanyl}-amino-4-acetoxy-azetidin-2-one;

(3S,4S)-3-{N-(3-phenylpropionyl)-N$^e$-nitro-L-arginyl}-amino-4-acetoxy-azetidin-2-one;

(3S,4S)-3-[2S-2-(3-phenylpropionoyl)amino-2-t-butyl-acetamido]-4-phenoxy-azetidin-2-one;

(3S,4S)-3-[2S-2-(3-phenylpropionoyl) amino-2-(3,4-dimethoxyphenyl) methyl-acetamido]-4-phenoxy-azetidin-2-one;

(3S,4S)-3-[2S-3-phenylpropionoyl) amino-2-(3,4-ethylenedioxyphenylmethyl)-acetamido]4-phenoxy-azetidin-2-one;

(3S, 4S)-3-[2S-2-benzyloxycarbonylamino-2-(3-benzothienylmethyl)-acetamido]-4-phenoxy-azetidin-2-one;

(3S,4S)-3-[2S-2-benzyloxycarbonylamino-2-(4,4'-biphenylmethyl)-acetamido]-4-phenoxy-azetidin-2-one;

(3S, 4S)-3-[2S-2-benzyloxycarbonylamino-2-(2-chlorophenylmethyl)-acetamido]-4-phenoxy-azetidin-2-one;

(3S, 4S)-3-[2S-2-benzyloxycarbonylamino-2-(4-chlorophenylmethyl)-acetamido]-4-phenoxy-azetidin-2-one;

(3S,4S)-3-[2S-2-benzyloxycarbonylamino-2-(3,4-dichloro-acetamido]-4-phenoxy-azetidin-2-one;

(3S, 4S)-3-[2S-2-benzyloxycarbonylamino-2-(2-fluorophenylmethyl)-acetamido]-4-phenoxy-azetidin-2-one;

(3S, 4S)-3-[2S-2-benzyloxycarbonylamino-2-(4-fluorophenylmethyl)-acetamido]4-phenoxy-azetidin-2-one;

(3S,4S)-3-[2S-2-benzyloxycarbonylamino-2-(3,4-difluoro-phenylmethyl)-acetamido]-4-phenoxy-azetidin-2-one;

(3S,4S)-3-[2S-2-benzyloxycarbonylamino-2-(4-iodo-phenylmethyl)-acetamido]-4-phenoxy-azetidin-2-one;

(3S ,4S)-3-[2S-2-benzyloxycarbonylamino-2-(naphth-1-yl)methyl)-acetamido]-4-phenoxy-azetidin-2-one;

(3S,4S)-3-[2S-2-benzyloxycarbonylamino-2-(4-nitro-phenylmethyl)-acetamido]-4-phenoxy-azetidin-2-one;

(3S,4S)-3-[2S-2-benzyloxycarbonylamino-2-(pentafluorophenyl-methyl)-acetamido]-4-phenoxy-azetidin-2-one;

(3S,4S)-3-[2S-2-benzyloxycarbonylamino-2-(4-thiazolylmethyl)-acetamido]-4-phenoxy-azetidin-2-one;

(3S,4S)-3-[2S-2-benzyloxycarbonylamino-2-(3-trifluoromethylphenyl-acetamido]-4-phenoxy-azetidin-2-one;

(3S,4S)-3-[2S-2-(3-phenylpropionoyl) amino-2-(3,4-methylenedioxyphenylmethyl)-acetamido]4-phenoxy-azetidin-2-one; and (3S,4S)-3-[2S-2-(3-phenylpropionoyl) amino-2-(3,4-diisopropyloxyphenylmethyl)-acetamido]-4-phenoxy-azetidin-2-one;

and salts thereof.

11. A pharmaceutical composition comprising a compound or salt as recited in claim 1 and a pharmaceutically acceptable carrier.

12. A method of treatment of osteoporosis, comprising administering to a patient in need of said treatment a pharmaceutical composition comprising a compound or salt as recited in claim 1 in an amount effective for treating said osteoporosis, and a pharmaceutically acceptable carrier.

13. A method of treatment of muscular dystrophy, comprising administering to a patient in need of said treatment a pharmaceutical composition comprising a compound or salt as recited in claim 1 in an amount effective for treating said muscular dystrophy, and a pharmaceutically acceptable carrier.

14. A method of treatment of cancer metastasis, comprising administering to a patient in need of said treatment a pharmaceutical composition comprising a compound or salt as recited in claim 1 in an amount effective for treating said cancer metastasis, and a pharmaceutically acceptable carrier.

15. A method of treatment of myocardial infarction, comprising administering to a patient in need of said treatment a pharmaceutical composition comprising a compound or salt as recited in claim 1 in an amount effective for treating said myocardial infarction, and a pharmaceutically acceptable carrier.

16. A method of treatment of inflammatory disease in a patient in need of such treatment, comprising administering to said patient a pharmaceutical composition comprising a compound or salt as recited in claim 1 in an amount which is effective for treating inflammatory disease, and a pharmaceutically acceptable carrier.

17. A method of treatment of arthritis in a patient in need of such treatment, comprising administering to said patient a pharmaceutical composition comprising a compound or salt as recited in claim 1 in an amount which is effective for treating arthritis, and a pharmaceutically acceptable carrier.

18. A method of treatment of pulmonary emphysema in a patient in need of such treatment, comprising administering to said patient a pharmaceutical composition comprising a compound or salt as recited in claim 1 in an amount which is effective for treating pulmonary emphysema, and a pharmaceutically acceptable carrier.

19. A method of treatment of septic shock in a patient in need of such treatment, comprising administering to said patient a pharmaceutical composition comprising a compound or salt as recited in claim 1 in an amount which is effective for treating septic shock, and a pharmaceutically acceptable carrier.

20. A method of treatment of cerebral ischemia in a patient in need of such treatment, comprising administering to said patient a pharmaceutical composition comprising a compound or salt as recited in claim 1 in an amount which is effective for treating cerebral ischemia, and a pharmaceutically acceptable carrier.

21. A method for improvement of memory function in a patient in need of such improvement, comprising administering to said patient a pharmaceutical composition comprising a compound or salt as recited in claim 1 in an amount which is effective for improving memory function, and a pharmaceutically acceptable carrier.

22. A method of treatment of parasitic infection in a patient in need of such treatment, comprising administering to said patient a pharmaceutical composition comprising a compound or salt as recited in claim 1 in an amount which is effective for treating parasitic infection, and a pharmaceutically acceptable carrier.

23. A method of treatment of cataract in a patient in need of such treatment, comprising administering to said patient a pharmaceutical composition comprising a compound or salt as recited in claim 1 in an amount which is effective for treating cataract, and a pharmaceutically acceptable carrier.

24. A method of treatment of malaria in a patient in need of such treatment, comprising administering to said patient a pharmaceutical composition comprising a compound or salt as recited in claim 1 in an amount which is effective for treating malaria, and a pharmaceutically acceptable carrier.

25. A method of treatment of glomerular basement membrane degradation in a patient in need of such treatment, comprising administering to said patient a pharmaceutical composition comprising a compound or salt as recited in claim 1 in an amount which is effective for treating glomerular basement membrane degradation, and a pharmaceutically acceptable carrier.

26. A method of treatment of viral infection in a patient in need of such treatment, comprising administering to said patient a pharmaceutical composition comprising a compound or salt as recited in claim 1 in an amount which is effective for treating viral infection, and a pharmaceutically acceptable carrier.

27. A method of regulating cysteine protease in a patient in need of such regulating, comprising administering to said patient a pharmaceutical composition comprising a compound or salt as recited in claim 1 in an amount which is effective for treating regulating cysteine protease, and a pharmaceutically acceptable carrier.

28. A method of preparing a compound of formula I, comprising reacting a compound according to formula II with a compound of the formula $R_3$-OH acid in presence of at least one member selected from the group consisting of dicyclohexylcarbodiimide and acid chloride in the presence of at least one member selected from the group consisting of base and activated ester:

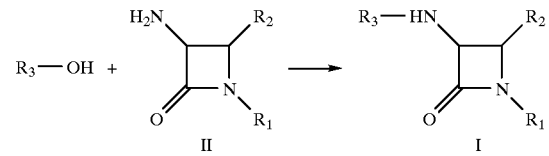

wherein
$R_1$ is
hydrogen; or
—$SO_3^- M^+$ wherein M is a hydrogen atom, a metal ion which is selected from sodium, potassium, magnesium, and calcium, or $N^+(R_4)_4$ wherein $R_4$ is a $C_1$–$C_6$ alkyl group, $R_2$ is
(a) a group —$OCOR_5$ wherein $R_5$ is
  (i) a $C_1$–$C_6$ alkyl group,
  (ii) a $C_2$–$C_6$ alkenyl group,
  (iii) a $C_2$–$C_6$ alkynyl group,
  (iv) a $C_3$–$C_6$ cycloalkyl group,
  (v) a phenyl group,
  (vi) a naphthyl group, or
  (vii) a monocyclic or bicyclic heterocyclic group, which group (i), (ii), (iii), (iv), (v), (vi), or (vii) is unsubstituted or substituted by 1, 2 or 3 substituents independently selected from
    hydroxy,
    halogen,
    carboxy,
    $C_1$–$C_4$ alkyl (which is unsubstituted or substituted at least once with carboxy and/or amino),
    $C_1$–$C_2$ alkoxy,
    amino,
    cyano, and
    phenyl and monocyclic or bicyclic heterocyclic groups, which phenyl and heterocyclic groups are unsubstituted or substituted by 1 or 2 substituents independently selected from
      hydroxy,
      halogen,
      carboxy,
      $C_1$–$C_4$ alkyl,
      $C_1$–$C_2$ alkoxy,
      amino, and
      cyano;
or (b) a group —$XR_5$ wherein X is selected from the group consisting of O, S, SO, and $SO_2$, and $R_5$ is as defined above;

$R_3$ is selected from the group consisting of D- or L-t-butyl alanine, D- or L-homophenyl alanine, D- or L-pyridyl alanine, D- or L-thienyl alanine, D- or L-naphthyl alanine, D- or L-methoxy phenyl alanine, D- or L-halo phenyl alanine, D- or L-ε-nitro arginine, D- or L-citrulline, D- or L-2-indoline carboxylic acid, D- or L-4-hydroxy-3-nitro-phenylalanine, D- or L-4-amino-3,5-diiodophenylalanine, D- or L-4-hydroxy-3,5-diiodo-phenylalanine, D- or L-4-hydroxy-3,5-dibromo-phenylalanine, D- or L-β-(3-benzothienyl)-alanine, D- or L-3,4(methylenedioxy)phenylalanine, D- or L-3,4 (ethylenedioxy)phenylalanine, D- or L-4,4'-biphenylalanine, D- or L-3,4-dichlorophenylalanine, D- or L-4-iodophenylalanine, D- or L-4-nitrophenylalanine, D- or L-pentafluorophenylalanine, D- or L-4-thiazolylalanine, D- or L-3-trifluoromethylphenylalanine, D- or L-4-trifluoromethylphenylalanine, D- or L-3-sulfamoyl-alanine, D- or L-t-butyloxy alanine, D- or L-1-t-butyloxymethylalanine, and D- or L-3,4-diisopropyloxyphenylalanine, in which the $NH_2$ of any of the above groups is unsubstituted or substituted once or twice with $R_7$ wherein $R_7$ is —$COOR_5$, —$COR_5$, —$SO_2R_5$, or —$COR_{14}$ wherein $R_5$ is as defined above and $R_{14}$ is amino group which is unsubstituted or substituted at least once with $C_1$–$C_6$ alkyl group which is unsubstituted or substituted at least once with 1 or 2 substitutents selected from hydroxy, halogen, cyano, amino, heterocycle, and phenyl (wherein the heterocycle or phenyl is unsubstituted or substituted at least once by 1 or 2 substituents selected from halogen, hydroxy, cyano, carboxy and amino).

29. A method of preparing a compound of formula I, comprising reacting a compound according to formula II with a compound of the formula $R_3$-OH acid in presence of at least one member selected from the group consisting of dicyclohexylcarbodiimide and acid chloride in the presence of at least one member selected from the group consisting of base and activated ester:

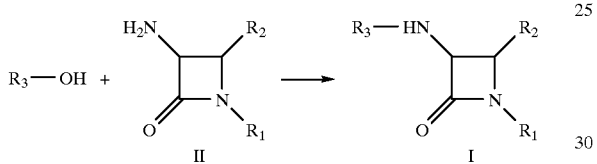

wherein
$R_1$ is
  hydrogen; or
  —$SO_3^-M^+$ wherein M is a hydrogen atom, a metal ion which is selected from sodium, potassium, magnesium, and calcium, or $N^+(R_4)_4$ wherein $R_4$ is a $C_1$–$C_6$ alkyl group;
$R_2$ is
  —$OCOR_5$ wherein $R_5$ is (i) a $C_1$–$C_6$ alkyl group which is unsubstituted or substituted at least once by 1 or 2 substitutents selected from hydroxy, halogen, and amino, or (ii) a phenyl group which is unsubstituted or substituted at least once by 1–3 substituents selected from hydroxy, halogen, $C_1$–$C_4$ alkyl group, $C_1$–$C_2$ alkoxy group, and cyano; or
  —$XR_6$ wherein X is O, S, SO, or $SO_2$; $R_6$ is (i) a $C_1$–$C_6$ alkyl group which is unsubstituted or substituted at least once by 1 or 2 substitutents selected from hydroxy, halogen, amino and phenyl (ii) a $C_3$–$C_6$ cycloalkyl group, (iii) a phenyl group which is unsubstituted or substituted at least once by 1–3 substituents selected from hydroxy, halogen, carboxy, $C_1$–$C_4$ alkyl group (which is unsubstituted or substituted with carboxy, amino or both), $C_1$–$C_2$ alkoxy group, cyano and heterocycle group, or (iv) naphthyl group which is unsubstituted or substituted at least once by 1–3 substituents selected from hydroxy, halogen, carboxy, $C_1$–$C_4$ alkyl group (which is unsubstituted or substituted at least once with carboxy, amino or both), $C_1$–$C_2$ alkoxy group and cyano;

$R_3$ is selected from the group consisting of D- or L-t-butyl alanine, D- or L-homophenyl alanine, D- or L-pyridyl alanine, D- or L-thienyl alanine, D- or L-naphthyl alanine, D- or L-methoxy phenyl alanine, D- or L-halo phenyl alanine, D- or L-ε-nitro arginine, D- or L-citrulline, D- or L-2-indoline carboxylic acid, D- or L-4-hydroxy-3-nitro-phenylalanine, D- or L-4-amino-3,5-diiodophenylalanine, D- or L-4-hydroxy-3,5-diiodo-phenylalanine, D- or L-4-hydroxy-3,5-dibromo-phenylalanine, D- or L-β-(3-benzothienyl)-alanine, D- or L-3,4(methylenedioxy)phenylalanine, D- or L-3,4 (ethylenedioxy)phenylalanine, D- or L-4,4'-biphenylalanine, D- or L-3,4-dichlorophenylalanine, D- or L-4-iodophenylalanine, D- or L-4-nitrophenylalanine, D- or L-pentafluorophenylalanine, D- or L-4-thiazolylalanine, D- or L-3-trifluoromethylphenylalanine, D- or L-4-trifluoromethylphenylalanine, D- or L-3-sulfamoyl-alanine, D- or L-t-butyloxy alanine, D- or L-1-t-butyloxymethylalanine, and D- or L-3,4-diisopropyloxyphenylalanine, in which the $NH_2$ of any of the above groups is unsubstituted or substituted once or twice with $R_7$ wherein $R_7$ is —$COOR_8$ wherein $R_8$ is a $C_1$–$C_6$ alkyl group which is unsubstituted or substituted at least once with phenyl group,
—COR, wherein $R_9$ is
  (i) a $C_1$–$C_6$ alkyl group which is unsubstituted or substituted at least once by 1 or 2 substitutents selected from hydroxy, halogen, cyano, amino, heterocycle, or phenyl (wherein the heterocycle or phenyl is unsubstituted or substituted at least once by 1 or 2 substituents selected from halogen, hydroxy, cyano, carboxy and amino); (ii) a heterocycle which may be mono or bicyclic or (iii) amino group which is unsubstituted or substituted at least once with $C_1$–$C_6$ alkyl group which is unsubstituted or substituted at least once with 1 or 2 substitutents selected from hydroxy, halogen, cyano, amino, heterocycle, and phenyl (wherein the heterocycle or phenyl is unsubstituted or substituted at least once by 1 or 2 substituents selected from halogen, hydroxy, cyano, carboxy and amino); or
$SO_2R_{10}$ wherein $R_{10}$ is
  (i) a $C_1$–$C_6$ alkyl group (ii) a $C_2$–$C_4$ alkenyl group which is unsubstituted or substituted at least once with heterocycle or phenyl, or (iii) a phenyl group which is unsubstituted or substituted at least once by 1–3 substituents selected from hydroxy, halogen, carboxy, $C_1$–$C_4$ alkyl group, $C_1$–$C_2$ alkoxy group and cyano.

* * * * *